(12) United States Patent
Fennington, Jr. et al.

(10) Patent No.: US 8,470,562 B2
(45) Date of Patent: Jun. 25, 2013

(54) IRX-2 MODIFIED MANUFACTURING PROCESS

(75) Inventors: George J. Fennington, Jr., Huntington Station, NY (US); Harvey J. Brandwein, East Hills, NY (US)

(73) Assignee: IRX Therapeutics, Inc., New York, NY (US)

( * ) Notice: Subject to any disclaimer, the term of this patent is extended or adjusted under 35 U.S.C. 154(b) by 0 days.

(21) Appl. No.: 12/423,601

(22) Filed: Apr. 14, 2009

(65) Prior Publication Data

US 2009/0258395 A1 Oct. 15, 2009

Related U.S. Application Data

(60) Provisional application No. 61/044,674, filed on Apr. 14, 2008.

(51) Int. Cl.
*A61K 38/19* (2006.01)

(52) U.S. Cl.
USPC ....... 435/70.4; 435/70.1; 435/70.3; 435/70.5; 424/85.1; 424/85.2; 424/85.4; 424/85.5

(58) Field of Classification Search
None
See application file for complete search history.

(56) References Cited

U.S. PATENT DOCUMENTS

| 4,390,623 | A | * | 6/1983 | Frabricius et al. | 435/70.4 |
|---|---|---|---|---|---|
| 5,662,899 | A | * | 9/1997 | Chokri et al. | 424/93.7 |
| 5,698,194 | A | * | 12/1997 | Hadden | 424/85.1 |
| 2004/0001829 | A1 | * | 1/2004 | June et al. | 424/144.1 |
| 2006/0165667 | A1 | * | 7/2006 | Laughlin et al. | 424/93.21 |
| 2007/0003430 | A1 | * | 1/2007 | Kaiser et al. | 422/24 |
| 2007/0025958 | A1 | * | 2/2007 | Hadden | 424/85.1 |
| 2007/0259330 | A1 | * | 11/2007 | Goddard et al. | 435/2 |

* cited by examiner

*Primary Examiner* — Daniel C Gamett
(74) *Attorney, Agent, or Firm* — Wolf, Greenfield & Sacks, P.C.

(57) ABSTRACT

A highly efficient method of making a primary cell derived biologic by purifying mononuclear cells (MNCs) in a automated cell processor to remove contaminating cells by loading leukocytes onto lymphocyte separation medium (LSM) and centrifuging the medium to obtain purified MNCs, storing the MNCs overnight in a closed sterile bag system, stimulating an induction mixture of the MNCs with phytohemagglutinin (PHA) or other mitogen and ciprofloxacin in a scalable cell culture device and producing a primary cell derived biologic from the MNCs, removing the mitogen from the induction mixture by filtering, incubating the induction mixture, clarifying the induction mixture by filtering to obtain a primary cell derived biologic supernatant, and clearing the primary cell derived biologic supernatant from adventitious agents by anion exchange chromatography, filtration. A closed system prevents contamination of the resulting primary cell derived biologic. An automated method of purifying cells. A method of scalably inducing cells.

17 Claims, 20 Drawing Sheets

| Current Process | Process Step | Modified Process |
|---|---|---|
| Single donor layered manually on LSM | Stage 1<br>LSM gradient | Cobe® 2991™ - donor pool of 12 |
| Manual centrifugation and pipetting | Stage 2<br>MNC washing<br>(LSM Removal) | Cobe® 2991™ - programmed wash cycles |
| Polypropylene tubes | Stage 3<br>MNC storage | VueLife® FEP bags |
| Collect 24 individual donor in PP tubes | Stage 4<br>Pool MNC | Collect from 2-3 donor pools in VueLife® FEP bags |
| Nunc Cell Factory™ at 37°C 5% $CO_2$ | Stage 5<br>Incubate 2 hr<br>(+ PHA/Cipro) | Nunc Cell Factory™ at 37°C 5% $CO_2$ |
| Manual centrifugation and pipetting | Stage 6<br>PHA washing | Spectrum® CellFlow Plus™ Hollow Fiber (TFF/diafiltration) |
| Cell Factory at 37°C 5% $CO_2$ | Stage 7<br>Incubate 24 hrs | Cell Factory at 37°C 5% $CO_2$ |
| Manual centrifugation | Stage 8<br>Supernatant Clarification | Pall Fluorodyne® II 0.45 micron filtration |
| Pall Fluorodyne® II 0.22μm Filtration | Stage 9<br>Pre-Filtration | Pall Fluorodyne® II 0.22μm Filtration |
| Pall Mustang Q® Anion Exchange | Stage 10<br>DNA Removal | Pall Mustang Q® Anion Exchange |
| Planova 15N Filtration | Stage 11<br>Viral Clearance | Planova 15N Filtration |

IRX-2 MODIFIED MANUFACTURING PROCESS

This application claims the benefit of priority under 35 U.S.C. Section 119(e) of U.S. Provisional Patent Application No. 61/044,674, filed Apr. 14, 2008, which is incorporated herein by reference.

BACKGROUND OF THE INVENTION

1. Field of the Invention

The present invention relates to a method of producing large-scale quantities of biologics. In particular, the present invention relates to a scaled-up process of manufacturing a primary cell derived biologic.

2. Description of Related Art

There are various methods in the art used to produce biologics from cells which generally involve the steps of stimulating cells through incubation and washing cells to obtain the desired product.

For example, U.S. Pat. No. 4,390,623 to Fabricius discloses a serum-free and mitogen-free T-cell growth factor (interleukin-2) preparation prepared from human, bovine, or porcine peripheral mononuclear blood cells which are washed several times with a liquid tissue culture medium and then stimulated in tissue culture medium supplemented with serum and mitogen. The separated stimulated cells are again washed with fresh tissue culture medium to remove substantially all of the serum and mitogen. The washed cells are suspended in fresh tissue culture medium and conditioned under incubation conditions to transfer the growth factor into the liquid. The tissue culture medium separated from the stimulated cells can be recycled to stimulate additional cells. The supernatant can be concentrated from 50 to 100-fold on an ultrafilter.

U.S. Pat. No. 4,406,830 to Fabricius discloses a process for producing serum-free, mitogen-free Interleukin-1 (Il-1) (also known as lymphocyte activating factor LAF) and serum-free, mitogen-free Il-2 by incubating peripheral mononuclear blood (PBL) cells in a serum-free liquid tissue culture medium to remove residual serum proteins on the surfaces of the PBL cells, activating the incubated cells with a mitogen, washing the activated cells with a sterile liquid to remove the mitogen from the cells and conditioning the serum-free mitogen-free activated cells in a liquid tissue culture medium to produce a serum-free, mitogen-free Interleukin-1 (IL-1), contacting the IL-1 containing liquid tissue culture medium with novel blood serum glycoprotein, and incubating the cells in the presence of IL-1 and the novel blood serum glycoprotein to induce synthesis of IL-2 and to transfer the IL-2 (T-cell growth factor) from the cells to the liquid phase of the tissue culture medium to thereby produce a serum-free, mitogen-free IL-2.

U.S. Pat. No. 5,503,828 to Testa discloses a method of large-scale production of alpha interferon through induction and purification. A mixture of alpha interferon subtypes produced from peripheral blood leukocytes is produced by (a) preparing human peripheral blood leukocytes by collecting buffy coats and lysing red blood cells with ammonium chloride; (b) suspending leukocytes at a cell density of 1–10×106 cells/ml in an induction medium, comprising Eagle's MEM containing Earle's Salts, L-glutamine, non-essential amino acids, 4.46 mg/ml Tricine, pH 7.4, 24 µg/ml neomycin sulfate, vitamins B3 and/or C, sodium bicarbonate, and between 0.1 to 1.5 mg/ml human agamma serum; (c) adding crude or purified alpha interferon as a primer to the leukocytes suspended in the induction medium; (d) incubating the suspension for a sufficient time at about 36 degrees C. while stirring at 100-300 rpm; (e) adding between 50-500 hemagglutinin units per ml of Sendai virus to the suspension; (f) incubating for a sufficient time at about 36 degrees C. while stirring at 100-300 rpm; (h) centrifuging at about 2,500 rpm to remove cells and debris; and (i) collecting crude alpha interferon as product, without ever separating one alpha interferon subtype from the other subtypes present in the alpha mixture.

U.S. Pat. No. 6,350,589 to Morris discloses a method of producing multisubtype Type 1 interferons. The method includes the steps of (a) culturing leukocytes; (b) stimulating the leukocytes to produce a crude interferon; (c) concentrating the crude interferon to remove low-molecular weight contaminants; (d) liquid volume to produce a concentrated crude interferon; (e) removing a substantial amount of serum albumin and other contaminants from the concentrated crude interferon to produce a partially purified interferon mixture containing a plurality of subtypes; (f) removing substantially all remaining serum albumin and other contaminants from the partially purified interferon mixture to generate an interferon mixture having a purity of between about 50% and about 80%; and (g) purifying the about 50% to about 80% interferon mixture to produce a highly purified mixture of Type I interferon having a purity of at least about 95% and containing no more than about 35% by weight IFN.alpha.-2 and IFN.alpha.-8 subtypes.

U.S. Pat. No. 6,896,879 to Talor discloses a method of producing a cytokine mixture that is serum-free, mitogen-free, and antibiotic-free. In the manufacturing process, mononuclear cells are separated from human donor "buffy coats" by step-gradient centrifugation and cultured with phytohemagglutinin (PHA) to enhance production and secretion of IL-2 and other cytokines from the donor white blood cells in culture. Subsequently, the culture supernatant is aseptically harvested, clarified and subjected to a commercial virus exclusion process. The supernatant is then further concentrated approximately 10 fold by ultrafiltration and microfiltration. At this point, Human Serum Albumin, Inj. USP is added and the concentrate is then buffered to a physiological pH and brought to a target IL-2 concentration per the label claim (example 400 IU/mL). The concentrate is then subjected to a second micro-filtration (0.22 micron-rated filter) and aseptically dispensed into sterile serum-type vials and labeled by its IL-2 content. Product potency is measured by the incorporation of radio-labeled thymidine by a cytotoxic T-lymphoid line (CTLL-2). The final injectable agent is further tested by ELISA for the presence of five marker cytokines: IL-2, IL-1β, GM-CSF, IFN-γ, and TNF-α.

U.S. Pat. Nos. 5,632,983; 5,698,194; 6,977,072; 7,153,499; 7,182,942 to Hadden disclose a method of producing a natural cytokine mixture (NCM) that is a unique cytokine mixture of IL-1β, IL-2, IL-6, IL-8, INF-γ, and TNF-α. Buffy coat white cells of human blood from multiple HIV-negative hepatitis virus-negative donors are collected. The cells from the donors are pooled and layered on ficoll hypaque gradients (Pharmacia) to yield lymphocytes free of neutrophils and erythrocytes. In a preferred embodiment for the production of NCM lymphocytes are washed and distributed in X vivo-10 media (Whittaker Bioproducts) to flasks (MicroCELLector™ T-25 Cell Culture Flasks) in which are immobilized stimulants, i.e. mitogens. The immobilization process for the stimulants is as described by the manufacturer for immobilizing various substances for panning procedures, i.e. separating cells, in the flasks. The cells are incubated for 24-48 hours in X vivo-10 media with 80 µg/ml ciprofloxacin (Miles Lab) at 37 degrees C. in a CO2/air incubator. Following incubation the supernatants are poured off and collected.

Human serum albumin (HSA) can be added to stabilize the interleukins. Generally the HSA is used at 0.1 to 0.5% (weight by volume). The supernatants are stored at 4 degrees C. to −70 degrees C. The pooled supernatants are characterized by measuring the cytokine content by bioassay for IL-2 and ELISAs for one or more of the interleukins IL-1-IL-15, CSFs, TNFs, and IFNs. Sterility is tested by culture in thioglycolate broth and endotoxin measured by limulus lysate assay as is known in the art. Each supernatant is standardized either by concentration or amount administered so that comparisons can be made. In particular the IL-2 equivalence for each supernatant is utilized. DNA and virus exclusion, if used, employs such techniques as ultrafiltration, ethanol fractionation, polyethylene glycol/bentonite precipitation, and/or solvent/detergent treatment as has been used for intravenous gamma globulin (IGIV News Update brochure). Photochemical inactivation, aluminum phthalocyanine, or gamma irradiation can be used. This process is further discussed in the present invention below.

There are several limitations of manual processes used for producing biologics such as operator sensitivity, potential for contamination in an open system, inconsistent ratios and total protein levels in the final product, all of which make the product unsuitable for pharmaceutical grade production. To deal with these problems in the past, cumbersome procedures were performed such as filters, starch, manual centrifugations, and washes. Previous processes were bench top procedures that produced inconsistent batches and small-scale quantities of product.

Another step in biologics processing that must be considered is the removal of viruses. Patient safety is paramount, and in biotechnology processes there is a risk of adventitious viruses contaminating the incoming cells. Accordingly, inactivation and removal steps are sought to remove viruses that may or may not be present. Several logs of clearance/inactivation are required, per FDA and ICH guidances. Regulatory agencies suggest testing of the unprocessed bulk for potential viruses as well including in the process methods which provide a minimum of 4 log10 of virus inactivation/removal to be considered significant. It is suggested the methods include two (or more) orthogonal steps preferably with one targeting non-enveloped viruses. The regulatory guidance suggests that validation studies should be conducted to characterize the ability of production methods to remove/inactivate adventitious viruses exhibiting a range of biochemical and biophysical properties to characterize the robustness of the process.

For primary cell derived biologic production donor leukocytes, source cells for cytokine production, are screened by the blood centers for presence of viral nucleic acid by PCR (NHCV and NHIV) and traditional viral antigens (human immunodeficiency virus (HIV), hepatitis C(HCV), hepatitis B (HBV) and human T-lymphotropic virus (HTLV)). However other viruses, Epstein Barr (EBV), Cytomegalovirus (CMV) and Human Parvovirus B-19 (B-19) may still be present in qualified donors and used for production. Detectable levels of EBV could be present in up to 100% of healthy donors (Walling et. al., 2003). B-19 levels in asymptomatic individuals have been reported to be greater than 1012 per mL (Doyle and Corcoran, 2006) and infection results in a brief period of viraemia with titers as high as 1014 per mL (Anderson 1985). Due to the extensive cell washing used in the primary cell derived biologic process, most plasma associated viruses are essentially removed from the donor leukocytes, and any virus detected virus in the primary cell derived biologic bulk, prior to downstream removal/inactivation steps, would only be those released from infected cells. Nevertheless, robust inactivation/removal processes are required to assure product safety.

The manual production process for the primary cell derived biologic is labor intensive and not readily amenable to scale-up and is limited to volumes of sterile fluid which could be handled by a manual process. Therefore, process development is sought to reduce manual manipulations, and achieve practicality for commercialization. Furthermore, a virus inactivation method is desired.

BRIEF SUMMARY OF THE INVENTION

The present invention provides for a method of making a primary cell derived biologic by purifying mononuclear cells (MNCs) to remove contaminating cells by loading leukocytes onto lymphocyte separation medium (LSM), and washing and centrifuging the medium to obtain purified MNCs with an automated cell processing and washing system, storing the MNCs overnight in a closed sterile bag system, stimulating an induction mixture of the MNCs with a mitogen and ciprofloxacin in a scalable cell culture system and producing a primary cell derived biologic from the MNCs in a scalable disposable cell culture device, removing the mitogen from the induction mixture by filtering, incubating the induction mixture, clarifying the induction mixture by filtering to obtain a primary cell derived biologic supernatant, and clearing the primary cell derived biologic supernatant from DNA and adventitious agents by applying anion exchange chromatography and 15 nanometer virus filtration with additional viral removal possible using ultraviolet-C (UVC).

The present invention also provides for an automated method of purifying cells by loading cells into an automated cell processor, washing and centrifuging the cells automatically, and obtaining purified cells.

The present invention further provides for a method of inducing cells by inducing cells in a scalable cell culture system.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings wherein:

FIG. 2 is chart comparing the manual versus the commercial scale primary cell derived biologic process of the present invention;

FIG. 7 is a photograph of the Cytokine Array primary cell derived biologic (commercial scale process);

DETAILED DESCRIPTION OF THE INVENTION

Figure 1:
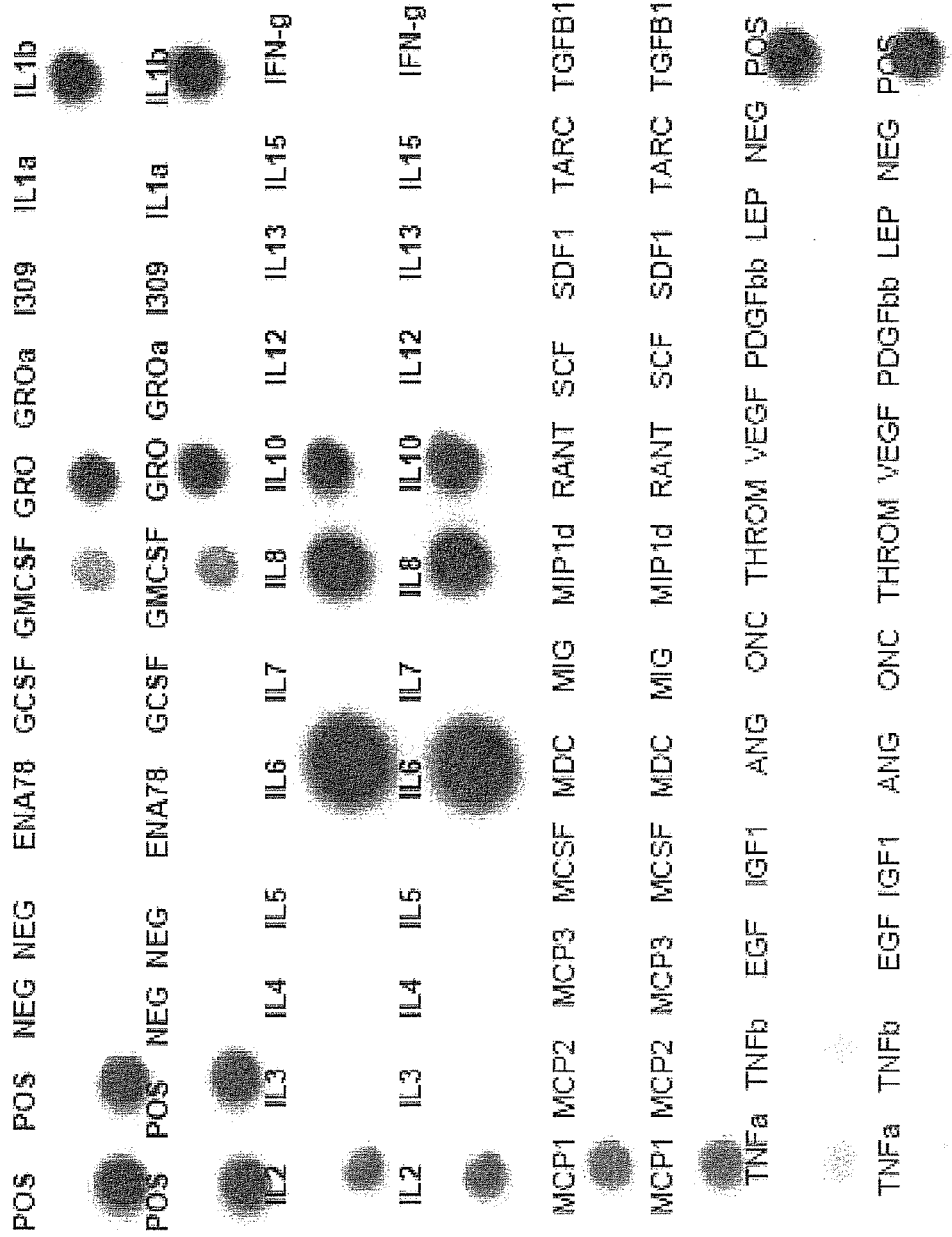
FIG. 1 is a photograph of the cytokine profile of the primary cell derived biologic that was used in Phase II clinical trials.

The present invention provides generally for a method of making large-scale quantities of a primary cell derived biologic, preferably IRX-2, for commercial production. The method makes novel use of several process steps that are scalable for desired product quantity. Mononuclear cells (MNCs) are purified to remove contaminating cells by loading leukocytes onto lymphocyte separation medium (LSM) and centrifuging the medium to obtain purified MNCs with an automated cell processing and washing system. The MNCs are then stored overnight in a FEP lymphocyte storage bag. An induction mixture of the MNCs is stimulated with a mitogen, preferably phytohemagglutinin (PHA), and ciprofloxacin in a disposable cell culture device and a primary cell derived biologic is produced from the MNCs. The mitogen is removed from the induction mixture by filtering and tangential flow filtration (TFF) mode, and then the induction mixture is incubated. The induction mixture is clarified by filtering to obtain a primary cell derived biologic supernatant. Finally, the primary cell derived biologic supernatant is cleared from DNA and adventitious agents by applying anion exchange chromatography and 15 nanometer filtration and optionally further inactivation by ultraviolet-C (UVC). The final product can then be vialed and stored for future administration to a patient.

A "primary cell derived biologic", as used herein, is a set of cytokines, preferably natural and non-recombinant cytokines, also previously known as an NCM (natural cytokine mixture). Preferably, the primary cell derived biologic is IRX-2 as described below, and the two terms can be used interchangeably throughout this application without derivation from the intended meaning.

"IRX-2" is a leukocyte-derived, natural primary cell derived biologic produced by purified human white blood cells (mononuclear cells) stimulated by phytohemagglutinin (PHA) and ciprofloxacin (CIPRO). The major active components are interleukin 1β (IL-1β), interleukin 2 (IL-2), and γ-interferon (IFN-γ). IRX-2 has also previously been referred to as an "NCM", a natural cytokine mixture, defined and set forth in U.S. Pat. Nos. 6,977,072 and 7,153,499. Briefly, IRX-2 is prepared in the continuous presence of a 4-aminoquinolone antibiotic and with the continuous or pulsed presence of a mitogen, which in the preferred embodiment is PHA. However, other mitogens can also be used. According to a preferred embodiment of the invention, the IRX-2 contains a concentration of IL-1β that ranges from 60-6,000 pcg/mL, more preferably, from 150-1,800 pcg/mL; a concentration of IL-2 that ranges from 600-60,000 pcg/mL, more preferably, from 3,000-12,000 pcg/mL, and a concentration of IFN-γ that ranges from 200-20,000 pcg/mL, more preferably, from 1,000-4,000 pcg/mL.

IRX-2 can also contain a concentration of IL-6 that ranges from 60-6,000 pcg/mL, more preferably, from 300-2,000 pcg/mL; a concentration of IL-8 that ranges from 6000-600,000 pcg/mL, more preferably from 20,000-180,000 pcg/mL; a concentration of TNF-α that ranges from 200-20,000 pcg/ml, more preferably, from 1,000-4,000 pcg/mL. Recombinant, natural or pegylated cytokines can be used or IRX-2 can include a mixture of recombinant, natural or pegylated cytokines. IRX-2 can further include other recombinant, natural or pegylated cytokines such as IL-12, GM-CSF (at a concentration that ranges from 100-10,000 pcg/mL, more preferably from 500-2,000 pcg/mL), and G-CSF.

For T-cells to become activated to kill neoplastic cells (e.g., head and neck cancer cells), a number of steps must occur. First, a cellular antigen recognizable to a T-cell must be presented to the T-cell. The lymph node contains antigen presenting cells (APCs) that perform this function. APCs are also identified as dendritic cells and are present in the stroma of the lymph node. Thus, the first step is antigen presentation by dendritic or APC cells. Second, TH1 cells must be developed that are specific to the antigen in question. Third, cytotoxic T-cells (CTL's) are "helped" to recognize and then attack the foreign cellular material bearing the antigen following mobilization from the lymph node to the site of invasion. Those TH cells that secrete cytokines interleukin 2 (IL-2) and interferon gamma (IFN-γ) are called TH1 cells and are associated with specifically stimulating CTL cytotoxic activity and cell-mediated immunity. Another class of T cells designated TH2 secrete primarily interleukins 4, (IL-4), 5 (IL-5), and 10 (IL-10) and promote the production of antibodies. The predominant "class" of cytokines (e.g., TH1 or TH2) produced at the outset of an immune response acts to "steer" the development of continued immune responses in part by inhibiting the production of the opposite type of cytokines. Thus, the immune response becomes "pointed" in either the TH1 (cell-mediated) or the TH2 (humoral) direction by the cytokine(s) present early on. For the initiation of a robust anti-tumor immune response, it is therefore crucial to have TH1-biased cytokines (e.g., IL-2, IFN-γ) present during the initial phase of the immune response. The goal in cancer immunotherapy has been to stimulate production of a sufficient number of tumor-specific cytotoxic T-cells to destroy the tumor.

IRX-2 is a cytokine product produced under pharmaceutical standards from phytohaemagglutinin and ciprofloxacin stimulated mononuclear cells obtained from normal, healthy blood donors. This product is intended to be injected locally subcutaneously to feed into the lymph nodes draining head and neck cancers for treatment of head and neck cancers. This product can also be used for any other type of cancer or infectious disease.

In the commercial IRX-2 process, the PHA, ciprofloxacin and cellular elements are removed through centrifugation and washing. The cell-free supernatant is further processed to clear adventitious agents (DNA, viruses) and then formulated, filter sterilized and vialed. Interleukin 2 (IL-2) is a major active cytokine component in IRX-2, along with gamma interferon (IFN-γ), interleukin 1 beta (IL-1β) and tumor necrosis factor alpha (TNF-α). These cytokines enhance cell-mediated immunity primarily as stimulators of the TH1 pathway. Analysis of IRX-2 also reveals the presence of other cytokine constituents at low levels, but these cytokines are considered to be not critical in the potency of the product.

These components act to enhance cell-mediated immunity by a variety of activities: recruitment of lymphocytes (primarily by IL-1β), up-regulation of lymphocyte growth receptors such as IL-2 receptor (IL-2R) (primarily by IL-1β, IL-2, IFN-γ), enhancing T cell proliferation (primarily by IL-1β, IL-2), maintaining a TH1 functional bias (primarily by IFN-γ), and enhancing the processing and presentation of (tumor) antigens by antigen presenting cells such as macrophages and dendritic cells (primarily by IFN-γ) which are important for full activation of T cells leading to tumor destruction. IRX-2 promotes the differentiation and maturation of dendritic cells. Mature dendritic cells are required to effectively present antigen to T cells. IRX-2 also induces the production of naïve T cells, which are capable of becoming specific upon presentation by a mature dendritic cell having antigen exposed thereon. TNF-α is not considered to be a primary active component clinically, but levels in IRX-2 are close to those of the foregoing; because of the high lability of TNF-α, its content is monitored as an indicator of product stability. Table 1 below provides a listing of concentrations for these cytokines in cGMP lots used in Phase I and Phase II Clinical trials.

TABLE 1

Primary Cytokine Components of IRX-2

| Description | IL-2 Bioassay (IU/mL) | Cytokines ELISA (pg/mL) | | | |
|---|---|---|---|---|---|
| | | IL-1β | IL-2 | IFN-γ | TNF-α |
| Manual | 76 | 418 | 5263 | 2028 | 1356 |
| Manual | 145 | 615 | 5797 | 1502 | 1815 |

Additional cytokines and chemokines in IRX-2 have been identified by ELISA. These include IL-6, IL-10, IL-12, IL-8, granulocyte colony stimulating factor (G-CSF) and granulocyte-macrophage colony stimulating factor (GM-CSF). The levels of these proteins are much lower than the concentrations of the primary active components except for IL-6 and IL-8. They are typically associated with the inflammatory response, and they are pleiotropic (i.e., have multiple mechanisms depending on the surrounding cells and cytokine milieu). Table 2 presents a listing of these cytokines and their levels in IRX-2.

TABLE 2

Primary Cytokine Components of IRX-2

| Description | Cytokines ELISA (pg/mL) | | | | | |
|---|---|---|---|---|---|---|
| | IL-6 | IL-8 | IL-10 | IL-12 | G-CSF | GM-CSF |
| Manual | 1487 | 20,689 | 109 | 15 | 152 | 579 |
| Manual | 4127 | 49,180 | 123 | 4 | 214 | 578 |

In addition to ELISA, RAYBIO Human Cytokine Array (Ray Biotech, Inc.) of the 42-most common cytokines provides a cytokine profile or "footprint" of the IRX-2 product. FIG. 1 shows the cytokine profile of the IRX-2 that was used in Phase II clinical trials.

The IRX-2 cytokine product contrasts with prior cytokine therapy in the following ways: (1) physiological rather than pharmacological doses are used; (2) the product is administered perilymphatically rather than intratumorally or intravenously; and, (3) production is from activated leukocytes rather than based upon recombinant technology in order to simulate endogenous cytokine levels from native activated cells.

The mode of delivery takes advantage of the normal afferent and efferent pathways of lymph node activation. Normally, lymphatics drain from an area of interest, such as a tumor bed, and antigens and other factors associated with disease migrate in the lymphatics to the regional nodes. At the regional nodes, antigen-presenting cells (APC or dendritic cells) are responsible for securing and processing these disease-related antigens and presenting them to T-cells, with resultant proliferation of activated, antigen-specific T-cells. By presenting the natural primary cell derived biologic at this location, rather than systemically, there is an opportunity to facilitate or mobilize dendritic cell function as well as directly activate T-cells to proliferate and become CTL cells. Additionally, by more direct application, lower drug exposures are permitted and less active cytokine drug substance is lost in systemic circulation.

Individual cytokine doses have been evaluated for toxicity in clinical trials and found to have typical dose-toxicity profiles. In contrast, cytokine dose-response curves are typically bell-shaped. Many cytokines are approved for human therapeutic use or have been evaluated in Phase I or Phase II clinical studies. When tested, the dose-toxicity profile of investigated cytokines has not been affected by concomitant administration of other cytokines. Based on the history of past use, a comparison chart of recommended or evaluated doses at the threshold of toxicity for various cytokines and the amount that cytokine present in a complete course of IRX-2 is shown in Table 3 along with the likely margin of safety in orders of magnitude as follows.

TABLE 3

Comparison of maximum IRX-2 cytokine doses vs. therapeutic doses

| Cytokine | Upper Limit New Specs. | Cumulative IRX-2 Dose with new upper limit specification | Therapeutic Dose (Systemic Administration) | Safety Margin (log scale) |
|---|---|---|---|---|
| IL-2 | 8000 pg/mL | [3]3360 IU | >1,000,000,000 IU | >6 |
| γ-IFN | 3800 pg/mL | [4]0.076 μg | 450 μg | >3.5 |
| IL-1β | 1400 pg/mL | [4]0.028 μg | 10 μg | >2.5 |
| TNF-α | 4300 pg/mL | [4]0.086 μg | 200 μg | >3 |
| IL-2 Bioactivity | 310 IU/mL | [4]6200 IU | >1,000,000,000 IU | >6 |

[3]Calculation: 8000 pg IL-2/mL × 0.021 IU/pg × 20 mL = 3360 IU
[4]New Specifications × (10 × 2) mL = cumulative IRX-2 maximum dose Given these safety margins, it is unlikely that significant toxicological impact would result from the doses of individual cytokines contained within IRX-2.

As used herein, "mononuclear cells" (MNCs) are cells of the hematopoietic system which do not contain granules. MNCs include lymphocytes, plasma cells, monocytes and macrophages, and mast cells.

As used herein, "adventitious agents" are viruses and toxins, and often infectious agents, which can accidentally contaminate a cell line. Adventitious agents in the present invention are desired to be removed from primary cell derived biologic before administration to a patient to reduce or eliminate chances of infection of unwanted diseases.

The process of the present invention is detailed in the right column of FIG. 2. Each of the steps in the process is amenable to scale-up for production of large quantities of the primary cell derived biologic.

In the first step of the process, the MNCs are purified to remove any cells that could be contaminating to the production of the primary cell derived biologic through the use of a cell processor, which is a programmable centrifugal device. This device is further described in the Examples below. The MNCs are enriched to be composed of lymphocytes and monocytes by loading the MNCs on Lymphocyte Separation Medium (LSM) and then centrifuging the MNCs. Preferably, 300 mL of LSM is used. The MNCs from donors are purified simultaneously, which means that multiple donors can be purified at once. Preferably, MNCs from 12 donors are simultaneously purified. The purification of cells by centrifuging of the MNCs is preferably at 1500 to 3000 rpm to optimize removal of granulocytes and red blood cells.

In general, the first step is an automated method of purifying cells by loading cells into an automated cell processor, washing and centrifuging the cells automatically, and obtaining purified cells. In other words, the automated method can be used for any cells for which purification is desired, and it is not limited to MNCs. Importantly, the use of the automated cell processor allows for scale-up or scale-down of the cells purified through adjusting specifications of the cell processor.

Such a purification process has previously been used to simply purify cells for subsequent use of the cells. It has not been used to produce cytokines and has not been used to produce natural cytokines.

The MNCs are then stored overnight in a closed sterile bag system. Preferably the bag is a fluorinated ethylene propylene (FEP) bag. The use of the bags in the present invention optimizes cytokine production above normal production levels. This is due to the rich $O_2$ environment in the bags which is optimal for cytokine production.

The next day, an induction mixture of the MNCs is stimulated with PHA for 2 hrs and ciprofloxacin for 2 hours at 37 C in 5% $CO_2$. Preferably, 80 μg/mL of ciprofloxacin are used. The induction occurs in a scalable cell culture device, which allows for greater quantities of mixtures to be induced than have previously been induced. Induction with the scalable cell culture device allows for the production of cytokines in greater quantities than have previously been induced in the manual method. Thus, in general, the present invention provides for a method of inducing cells by inducing cells in a scalable cell culture system. Cells can be induced to make any cellular product, such as the cytokines induced in the present invention. The process is not limited to induction of cytokines, and any desired product can be induced.

PHA is then removed from the induction mixture through filtering. More specifically, the induction mixture is washed with sterile saline, the MNCs are recovered, and then resuspended in culture medium with 80 μg/mL ciprofloxacin. Preferably, the level of PHA is reduced to less than <150 ng/mL. Preferably, the filter is the Spectrum® CellFlow Plus® Hollow Fiber filter, and operates in tangential flow mode. The incubation mixture is then incubated, preferably for 24 hours. Normally, cell washing processes are used to obtain cells to be used. The present invention uses washing to remove PHA but the cells are returned to the culture in order to produce further cytokines. The filters in this step and in each step of the process are scalable and any appropriate filter can be used. After 24 hours the primary cell derived biologic is produced comprised of type I (TH1) cytokines. The induction mixture is then clarified, i.e. harvested, to obtain the primary cell derived biologic supernatant from the MNCs. The cells are filtered with a fluorodyne membrane with a 0.45 μm filter. Preferably, the filter is a FLUORODYNE II™ (Pall) filter is used and further described in the Examples. This automatic step provides advantages over the previous manual centrifugation of the primary cell derived biologic.

The last step in the method of production is clearing the primary cell derived biologic supernatant from DNA and adventitious agents by applying anion exchange chromatography and 15 nanometer virus filtration. Additional viral inactivation can be achieved by applying UVC. Various adventitious agents can be cleared, as described above, such as viruses and DNA. Viruses cleared include, but are not limited to, human immunodeficiency virus (HIV), hepatitis C(HCV), hepatitis B (HBV), human T-lymphotropic virus (HTLV), simian virus 40 (SV40), porcine parvovirus (PPV), pseudorabies virus (PRV), hepatitis A (HAV), bovine viral diarrhea virus (BVDV), Sindbis, Reo and Adeno viruses. Preferably, the anion exchange and 15 nanometer virus filtration steps clear over 4 $\log_{10}$ viruses.

When UVC is applied, it is uniformly delivered to the primary cell derived biologic by spirally flowing the primary cell derived biologic supernatant along an UVC irradiation source. Preferably, the UVC is delivered at a wavelength of 254 nm of the primary cell derived biologic, and at a dose of up to 150 $J/m^2$.

Preferably, the unique primary cell derived biologic produced is IRX-2 (formerly known as NCM). The cytokines produced in IRX-2 include IL-1β, IL-2, and IFN-γ. Preferably, IL-2 and IL-1β are produced in a 10:1 ratio. Preferably, greater than 4 L of IRX-2 is produced total in a batch. Preferably, the primary cell derived biologic supernatant can be concentrated and formulated to 300-1800 pg/mL IL-1β, 4000-8000 pg/mL IL-2, 1000-3800 pg/mL IFN-γ, and 1000-4300 pg/mL TNF-α are produced. The induction mixture can be optionally actively gassed.

The data herein show that the IRX-2 process is significantly improved by the following process improvements: (1) MNC purification using the automated cell processor, (2) storage of MNCs in VUELIFE® (American Fluoroseal Corporation) FEP bags, (3) induction in a scalable cell culture device (4) cell washing using Hollow Fiber (HF) filter system and (5) culture supernatant clarification via filtration using a 0.45 μm filter, (6) DNA removal using anion exchange chromatography filtration, (7) virus removal using dual 15 nanometer filters in series, and (8) additional viral inactivation can be achieved by applying UVC. An assessment of each unit operation and its changes shows that the critical parameters are maintained within an acceptable working range and that the process is able to provide product meeting its specifications.

The commercial process was further evaluated by performing several batches with all of the process modifications which produced all of the IRX-2 cytokines in typical ratios as previously seen with the manual process. Comparability of the primary cell derived biologic components and biological equivalence were confirmed by the RAYBIO Human Cytokine Antibody Array (RayBiotech, Inc.) and the peptide conjugate vaccine model. Based on these data, the commercial process is comparable to the manual IRX-2 process and producing a consistent and reproducible product.

As shown in FIG. 2, developments/changes from the previous IRX-2 process were made in each of the following steps of manufacturing. First, in the purification step, there was a change from manual centrifugation to an automated cell processor. The overnight storage of the MNCs was changed from overnight storage of MNC in polypropylene tubes to storage of MNCs in VUELIFE® FEP bags. Cell washing was improved by changing from manual centrifugation to a Hollow Fiber (HF) filter system. Induction was improved and scalability of the process was achieved by using a disposable cell culture device (Cell Factory). Also, harvesting/clarification of the culture supernatant was improved by changing from manual centrifugation to single pass filtration using a 0.45 μm filter DNA removal was improved by filtration with anion exchange chromatography filters. Virus removal was improved by filtration with dual 15 nanometer filters in series. Further virus inactivation can be improved by applying UVC.

Due to these changes, the IRX-2 commercial manufacturing process has been improved over the previous manual process. Overall, a reduction of production time and effort by use of the automated cell processor removes much of the error and variation produced between batches of IRX-2 in the previous process. For example, operator error is reduced due to automation. Volume scale up is achieved due to the system design and automation. Furthermore, contamination is avoided because a closed bag system is used, affording aseptic processing, which is an immense advantage over the previous process. The advantages of the viral clearance are discussed below.

The commercial method of IRX-2 manufacture includes viral clearance by nanofiltration 15N filters in series as a dedicated virus removal step and also includes DNA removal by the disposable anion exchange chromatography unit. 15N filters have been shown to be highly effective in removal of human immunodeficiency virus type 1 (HIV-1), pseudorabies virus (PRV), hepatitis A virus (HAV), bovine viral diarrhea virus (BVDV) and porcine parvovirus (PPV) in studies performed by the manufacturer and end users. In contrast, anion exchange has been shown to be effective against select target viruses. It is strongly advised to have two orthogonal methods that are capable of removing or inactivating a variety of model viruses in order to best assure patient safety (FDA Points To Consider, 1993).

In order to add an additional viral clearance method to the IRX-2 process, UVC inactivation is added as an inactivation step in the present invention. As further discussed in the Examples below, studies were conducted over a wide range of UV doses from 20-150 J/m$^2$ and showed no significant change in cytokine content using cytokine ELISA, western blot, cytokine arrays or CTLL-2 bioassay. In addition a new bioassay for TNF-α was developed which measures bioactivity of this labile cytokine. Although some decrease in TNF-α bioactivity was detected, this loss was comparable to the loss typically seen in other processing steps. At these same UVC doses (100 J/m$^2$) greater than 4 $\log_{10}$ of viral inactivation was achieved for the model viruses, PPV and BVDV, and for the blood borne virus, HAV. HIV was minimally inactivated with <2 $\log_{10}$ of viral inactivation. Utilizing this UVC technology, multiple laboratory batches of IRX-2 were successfully produced at the current scale and passed bulk release specifications confirming the robustness of the UVC process. The improved process provides better protection of patients by including an inactivation step which is robust and can inactivate a wide range of viral contaminants including non-enveloped viruses such as hepatitis A and parvovirus B19 and enveloped viruses (hepatitis C virus).

The data in the Examples summarizes the development of a new viral inactivation technology, UVC irradiation, capable of complementing the viral clearance methods without significantly reducing IRX-2 cytokine yields. Based on these requirements and the source material, human leukocytes, inactivation of 4 $\log_{10}$ of the test viruses is the desired target for this additional procedure to be useful. UVC inactivation when combined with the two existing methods of viral clearance in the IRX-2 process, anion exchange and 15N filtration, could potentially increase the overall viral inactivation/removal to 12 or more $\log_{10}$ of non-enveloped viruses.

Development/changes in the IRX-2 process were made in the following steps of manufacturing: Cobe 2991 automated cell processing centrifugation, use of sterile bags for lymphocyte storage, induction in a disposable cell culture device, cell washing with hollow fiber filtration, DNA removal with anion exchange chromatography, viral removal with dual 15 nanometer filtration in series and additional viral inactivation by UVC. FIG. 2 illustrates the IRX-2 process with the addition of UVC viral inactivation.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLE 1

Purification of MNCs Using Cell Processor/FEP Bag Storage

LSM Fraction Studies

The purpose of the LSM purification step in the IRX-2 process is to remove contaminating cells (granulocytes, red blood cells and platelets) yielding an enriched preparation of mononuclear cells (MNCs) composed of lymphocytes and monocytes.

Granulocytes can cause poor cytokine yield by interfering with accurate cell counting of MNC as well as interfering with PHA induction (i.e. by binding PHA). The actual process limit of granulocytes has not yet been determined. Early in the process development of IRX-2, granulocyte removal was monitored on the Coulter Ac•T diff 2 hemocytology analyzer and the process limit was set at NMT 5% (limit of detection of the Ac•T diff 2).

In the previous process, MNCs are purified manually using centrifugation over Lymphocyte Separation Medium density gradients (LSM, equivalent to FICOLL-HYPAQUE 1077 (Sigma)). Each donation is purified separately and up to 24 donations are pooled just prior to cytokine induction. This results in high purity, but is not suited to scale up due to the limitation of manual processing which requires two operators a full 8-10 hr shift to process 24 donors (12 donors per operator).

In the modified process of the present invention, LSM purification is performed using a closed sterile bag system and a programmable centrifugal device, a cell processor. The commercial process allows the leukocytes to be processed in donor pools of 12. This allows one operator to process up to 36 donors per shift.

Figure 3:
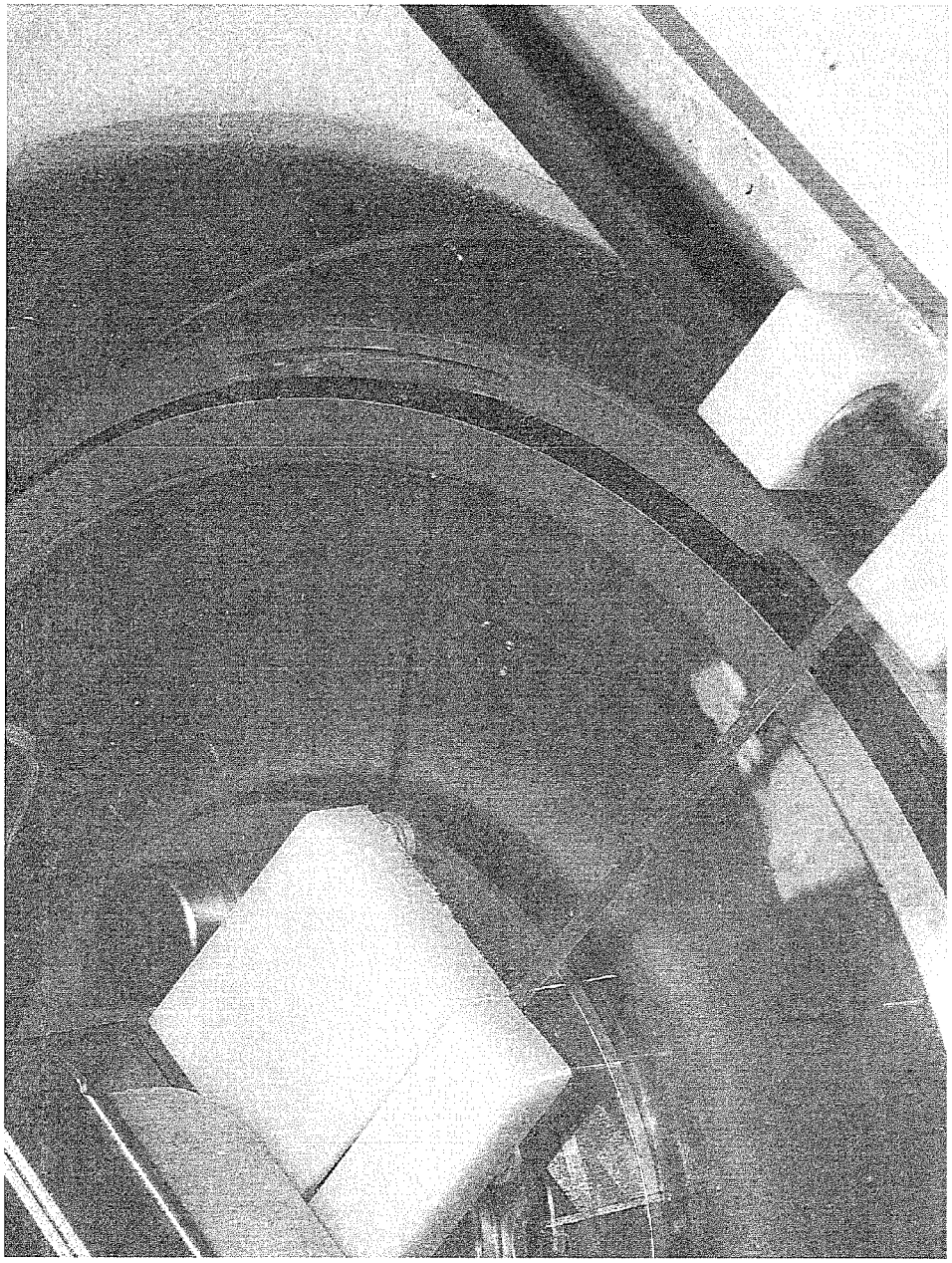
FIG. 3 is a photograph of centrifuging the buffy coat for 20 minutes.
Figure 4:
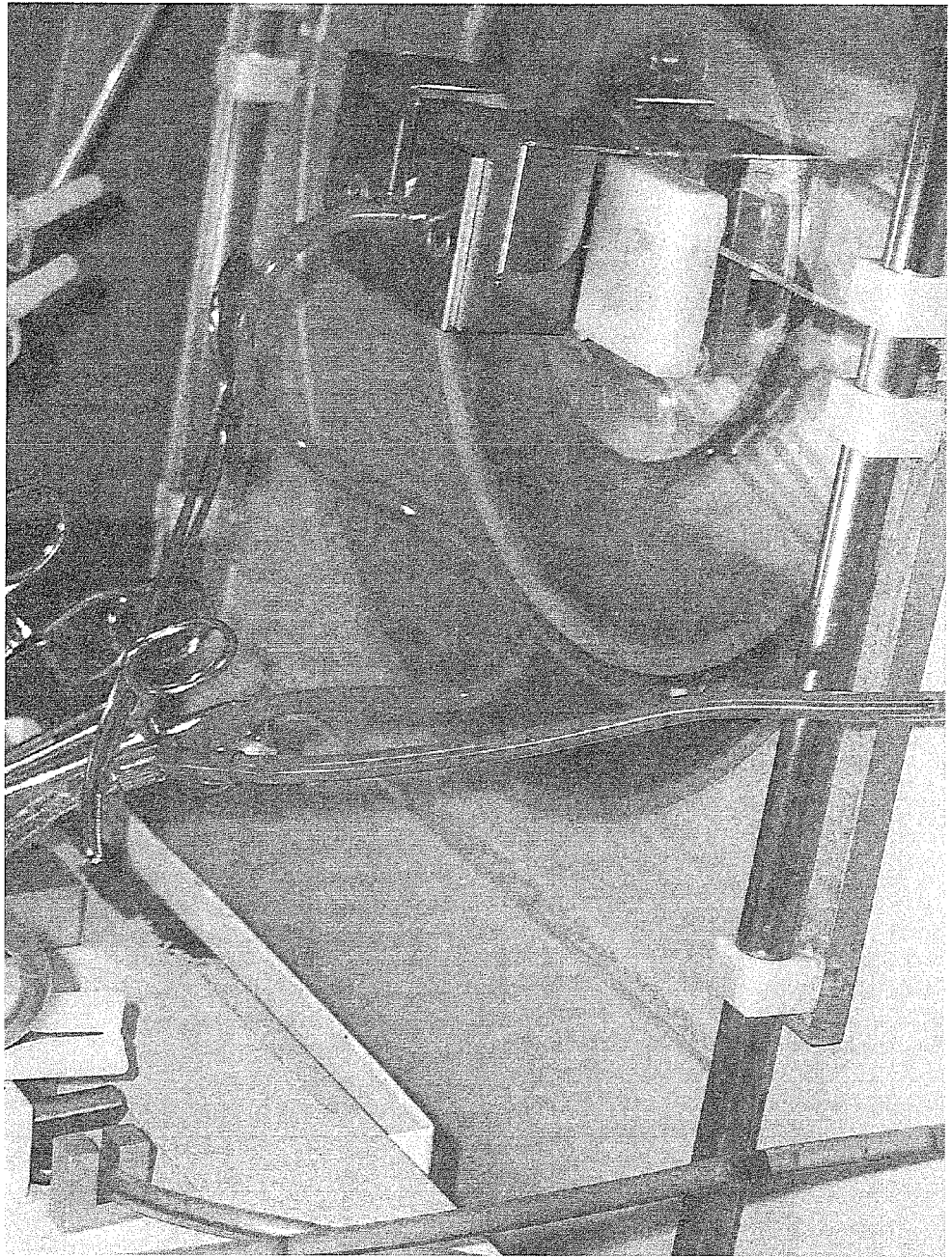
FIG. 4 is a photograph of separating out the MNCs.

In the commercial process, bags are aseptically filled and leukocytes are pooled. The leukocyte bags are aseptically attached to a harness. Leukocytes are pooled into a single bag and the bag is heat sealed. The bag is installed in the Cell Processor and valves and color-coded tubing is aligned. The leukocytes are loaded and centrifuged. A buffy coat is prepared, concentrated, and collected. A second bag is installed in the Cell Processor. The buffy coat is layered onto LSM at 20 mL/minute, and centrifuged for 20 minutes (FIG. 3). The MNCs are separated out into a third bag shown in FIG. 4. Cells are washed in the programmed wash cycles with saline and resuspended in serum-free culture media.

Results:

To analyze the feasibility of using the cell processor for LSM purification of MNCs, initial development of the procedure involved purifying MNCs via a cell processor and aseptically collecting the expressed cells in fractions. These fractions were analyzed via the Coulter Ac•T diff 2 analyzer and showed that the purified MNCs can be collected essentially free of granulocytes.

TABLE 4

Coulter Ac•T diff 2 analysis of collected MNC Fractions

| Fraction | Total Cells ($10^8$) | Volume (mL) | % Lymph | % Mono | % Grans |
|---|---|---|---|---|---|
| 1 | 0.075 | 25 | —n.d | — | — |
| 2 | 0.025 | 25 | — | — | — |
| 3* | 20 | 25 | 88 | 9 | 2.2 |
| 4* | 15 | 25 | 90 | 7.5 | 2.4 |
| 5* | 2.7 | 25 | 88 | 5.9 | 5.7 |
| 6* | 1.3 | 25 | 89 | 3.4 | 7.4 |
| 7 | 0.85 | 25 | 88 | 2.2 | 9.8 |
| 8 | 0.48 | 25 | 81 | 3.9 | 14.7 |
| 9 | 0.30 | 25 | 73 | 4.7 | 21.9 |
| 10 | 0.25 | 25 | — | — | — |

*pooled fractions;
n.d.none detected

Figure 5:
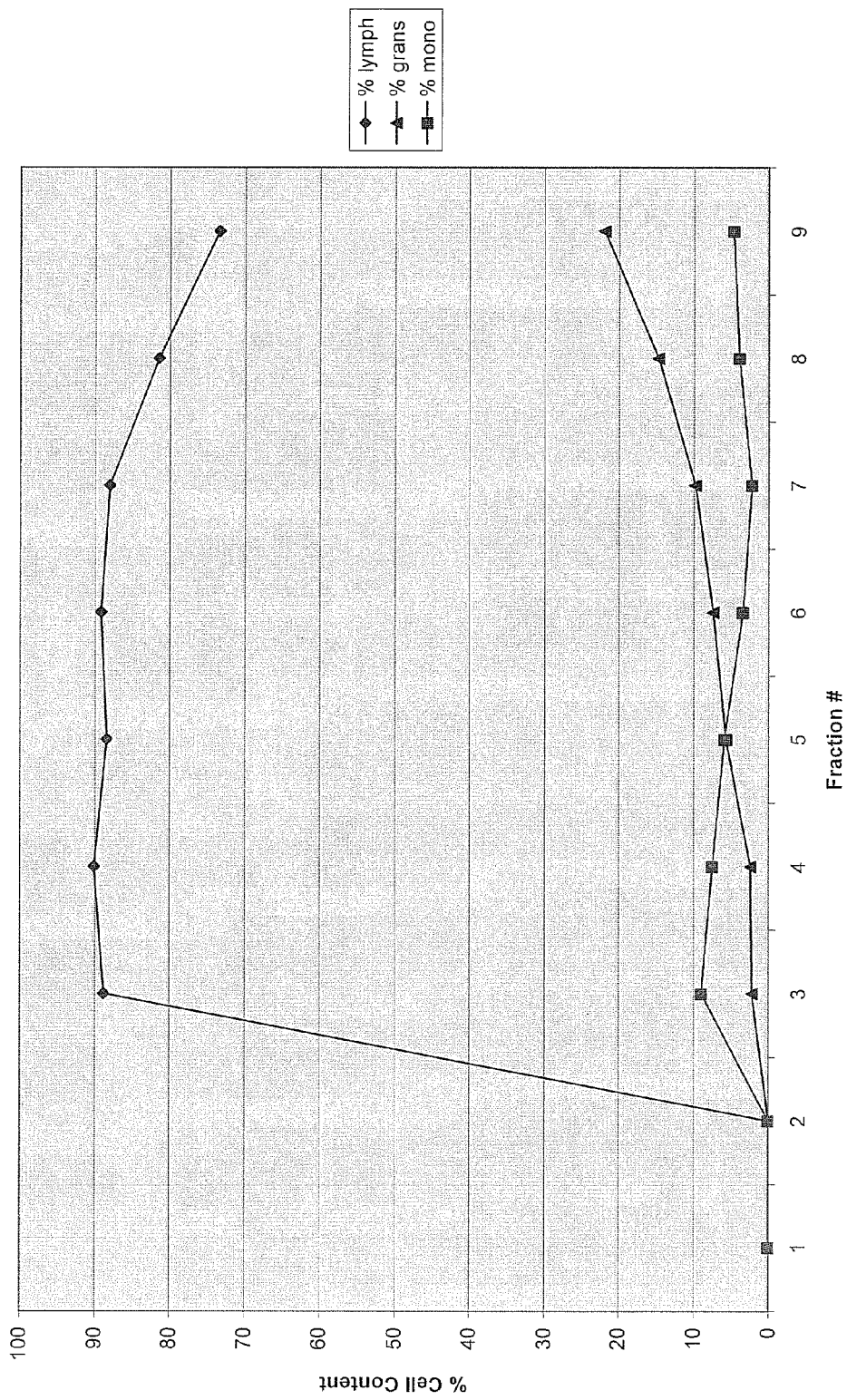
FIG. 5 is a graph of the Cell population analysis of cell processor purified MNCs via Ac•T diff2.

FIG. 5 and Table 4 show the relative cell distribution of the fractions collected from the cell processor This demonstrate the potential to collect up to 100 mL of MNCs from the cell processor that meet the required purity ($\leq$5% granulocytes), with a total yield of cells as high as $4 \times 10^9$ cells. This equates to a 10 fold increase of cells that can purified by a single operator. Fractions containing most of the MNC (Fractions 3-6) were aseptically collected, pooled and washed by the standard wash method and stored overnight in FEP bags The MNCs were used to produce an IRX-2 batch with the appropriate cytokine levels of IL-1β, IL-2 & IFN-γ for IRX-2 production.

MNC Storage Studies

In the previous process, purified MNCs are stored overnight in polypropylene centrifuge tubes. Due to the large volume of MNCs produced per run using the cell processor, an alternative to storage of 40 mL of individual donor MNCs (approx $5 \times 10^8$) in 200 mL polypropylene tubes was implemented. To accommodate the high yields of cells, (FEP) bags were used to store MNCs overnight (37° C., 5% $CO_2$). FEP bags storage bags have been utilized for expansion of dendritic cells, the storage of human lymphocytes and production of LAK cells and are suitable for lymphocytes storage due to the high gas permeability and low binding properties. To store the cells, the concentration in the FEP bags was adjusted to be equivalent to the storage concentration in polypropylene tubes. MNC viability and cell concentration were monitored using the GUAVA VIACOUNT (Guava Technologies).

Figure 6:
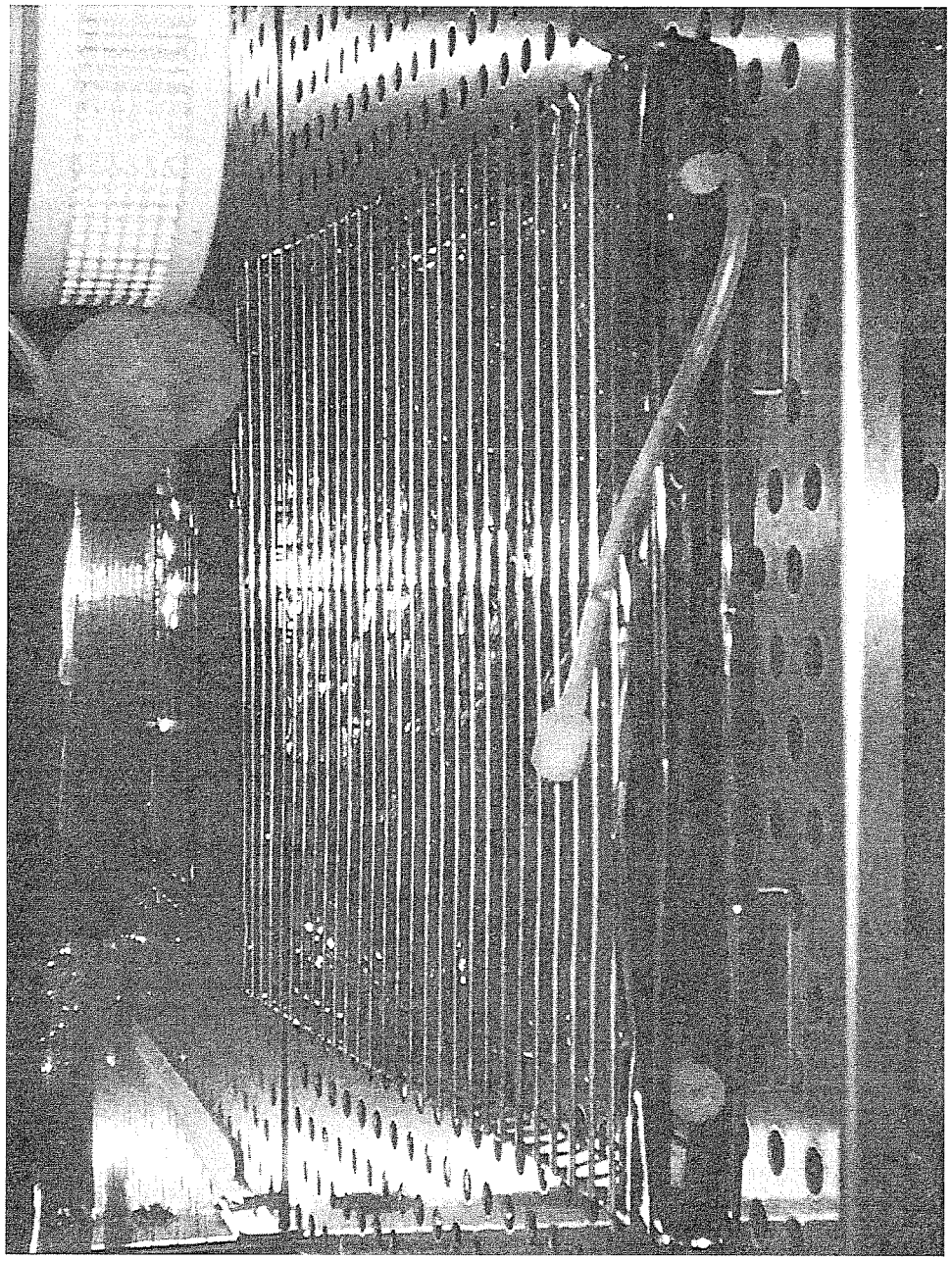
FIG. 6 is a photograph of storing the FEP bag overnight.

FIG. 6 shows the storage process. The MNCs are aseptically removed from their bag and aseptically transferred to the FEP bag. The FEP bags are stored overnight.

Results:

The overnight storage procedure was evaluated by comparing the cell concentration and viability for purified MNCs. Samples were evaluated by the Guava®Viacount® on Day 1 (at time of dilution into FEP bags and Day 2 (prior to PHA induction). As can be seen in Table 5, the MNCs showed no loss in cell concentration and retained high viability (95%) during the overnight storage demonstrating the suitability of the storage methods.

TABLE 5

Cell population analysis of cell processor purified MNCs via Viacount

| MNC Preparation | Viacount Day 1 | | Viacount Day 2 | |
|---|---|---|---|---|
| | cells/mL* ($\times 10^7$) | % viability | cells/mL+ ($\times 10^7$) | % viability |
| N = 20 | 1.9 ± 0.2 | 96 ± 2.1 | 1.9 ± 0.3 | 95 ± 3.5 | mean ± s.d.

Cell Type Characterization and Distribution Studies

To fully evaluate the MNCs produced on the cell processor, the various cell populations in the purified MNCs were examined to determine comparability of the cells produced by the new method versus the manual LSM purification. MNCs were analyzed using cell differentiation (CD) marker via fluorescence activated cell sorting (FACS) to quantitate the cell populations.

Results:

In Table 6, data on cell population distribution is presented both for MNCs prepared by the manual LSM purification method, as well as by the automated cell processor method.

For the original method, FACS analysis was performed on Day 2 pooled MNCs immediately prior to PHA induction. For the commercial process, cell populations were sampled and tested on both Day 1 (prior to overnight storage) and Day 2 (after overnight storage).

TABLE 6

Cell population analysis of cell processor purified MNCs via FACS

| Sample | CD14+/45+ Monocytes | CD14−/45+ Lymphocytes | CD15+ Granulocytes | CD3+ T cells | CD19+ B Cells | CD16/56+ NK Cells |
|---|---|---|---|---|---|---|
| Manual Process: Day 2 (n = 13*) | 18 ± 3 | 80 ± 4 | 1 ± 0.4 | 55 ± 4 | 7 ± 2 | 8 ± 2 |
| Commercial Process Day 1[2] (n = 25) | 18 ± 3 | 69 ± 6 | 2.2 ± 2.3 | 47 ± 8 | 9 ± 3 | 13 ± 3 |
| Commercial Process Day 2[2] (n = 25) | 12 ± 4 | 75 ± 5 | 1.7 ± 1.6 | 54 ± 5 | 8 ± 2 | 12 ± 4 |

Data presented as percent total cells (mean ± s.d), B

The data in Table 10 confirms the equivalence of the commercial process to the manual method. The resulting MNC preparations were produced with granulocyte content below the current specification of ≦5% as predicted in the available literature (Brutel de la Riviere et. al. 1977). This data indicates that the MNCs generated by the cell processor are equivalent in cell distribution and purity to the standard method.

It was observed that the monocyte concentration (CD14+/CD45+) appears to be consistently lower in the commercial process after incubation (Day 2) compared to the previous manual process method. Examination of the freshly prepared MNC (Day 1) revealed there was a slight drop in the monocyte marker (CD14+) population, from 18% to 12%.

The slight difference in the cell population was investigated further by determining the cell population of cell processor purified MNC immediately after processing and prior to the overnight incubation.

Table 10 shows that the mononuclear cells sampled immediately from the cell processor look comparable to that seen for the previous process. It is evident from these data that the time when the cells are sampled and analyzed has a large effect on the population profile. In the new process, cells sampled after the overnight storage have a slightly lower shift in the CD14+ CD45+ marker for monocytes. This change in the CD14+ CD45+ population can be attributed to the activation of monocytes with heterologous donor lymphocytes; this is termed a mixed lymphocyte reaction (MLR). According to the literature (Jordan & Ritter 2002), this reaction can prime the T cells to produce TH1 cytokines (i.e. IL-1β, TNF-α, and IFN-γ), which are the primary products of the IRX-2 process. Since these are desired in the product, holding the pool overnight shows no negative impact on IRX-2 production.

2-3 L Batch Studies

The purpose of this study was to produce several 2-3 L IRX-2 development batches utilizing cell processor purified MNCs. The purified MNCs cell preparations from several runs, performed on the same day were pooled to produce sufficient cells to produce a 10 stack cell culture device batch.

Results:

The equivalence of cytokine production from the commercial process was confirmed via numerous ELISA assays and the CTLL-2 bioassay. The final product ranges for the various cytokines were predicted by normalizing the cytokines to a target concentration of 7000 pg/mL of IL-2. As can be seen in Table 7, the bulk product produced could be formulated to pass all of the cytokine assays and are comparable to the Phase I and II clinical product.

Figure 7:
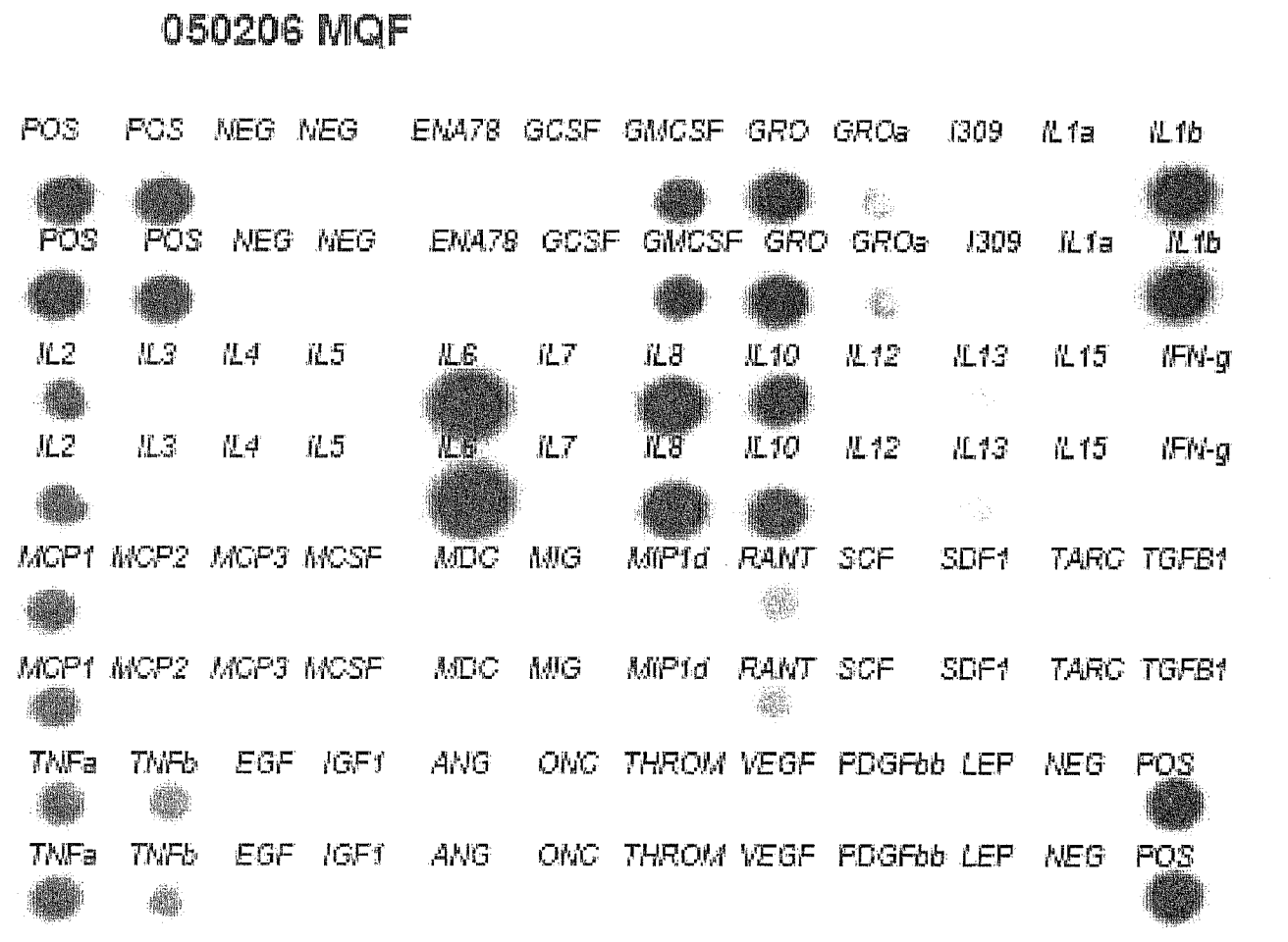

The main difference in the modified process is the resulting purified MNCs from multiple donors (monocytes, T cells, B cells and NK cells) are incubated together overnight prior to mitogen induction. To confirm no new species of cytokines are produced from this method, especially TH2 cytokines (i.e. IL-3, IL-4 & IL-5) and to prove the comparability of cytokine production from the cell processor generated MNCs, the modified process IRX-2 was analyzed via cytokine arrays (Array 3, RAYBIO Human Cytokine Antibody (RayBiotech, Inc.)) which detects 42 human cytokines, chemokines and growth factors. Array analysis of these most common cytokines (Huang et. al. 2001) on IRX-2 from cell processor generated cells confirmed that the commercial IRX-2 product profile or "footprint" is comparable in cytokine composition to the current product and no new cytokines are induced (i.e. Type 2 cytokines) as shown in FIG. 7.

EXAMPLE 2

Cell Washing Using the Hollow Filter System

An automated MNC wash method was developed, which effectively removes the process chemical phytohemagglutinin (PHA), a mitogen, from induced MNCs to levels comparable to washing by manual centrifugation while maintaining cell viability and the ability to produce IRX-2 cytokines.

Figure 8:
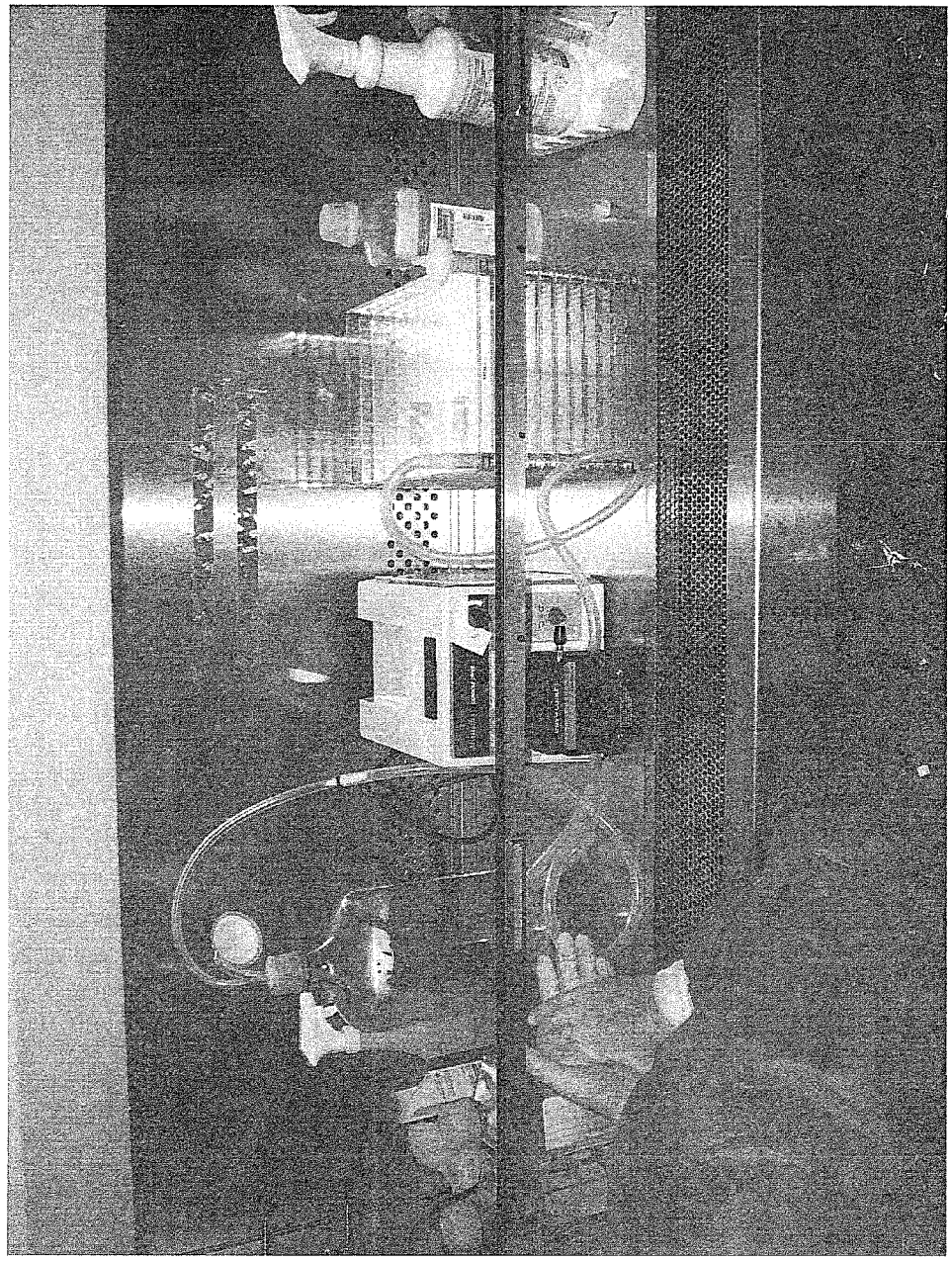
FIG. 8 is a photograph of the cells being mixed with media/inducers and being transferred to a disposable cell culture device.
Figure 9:
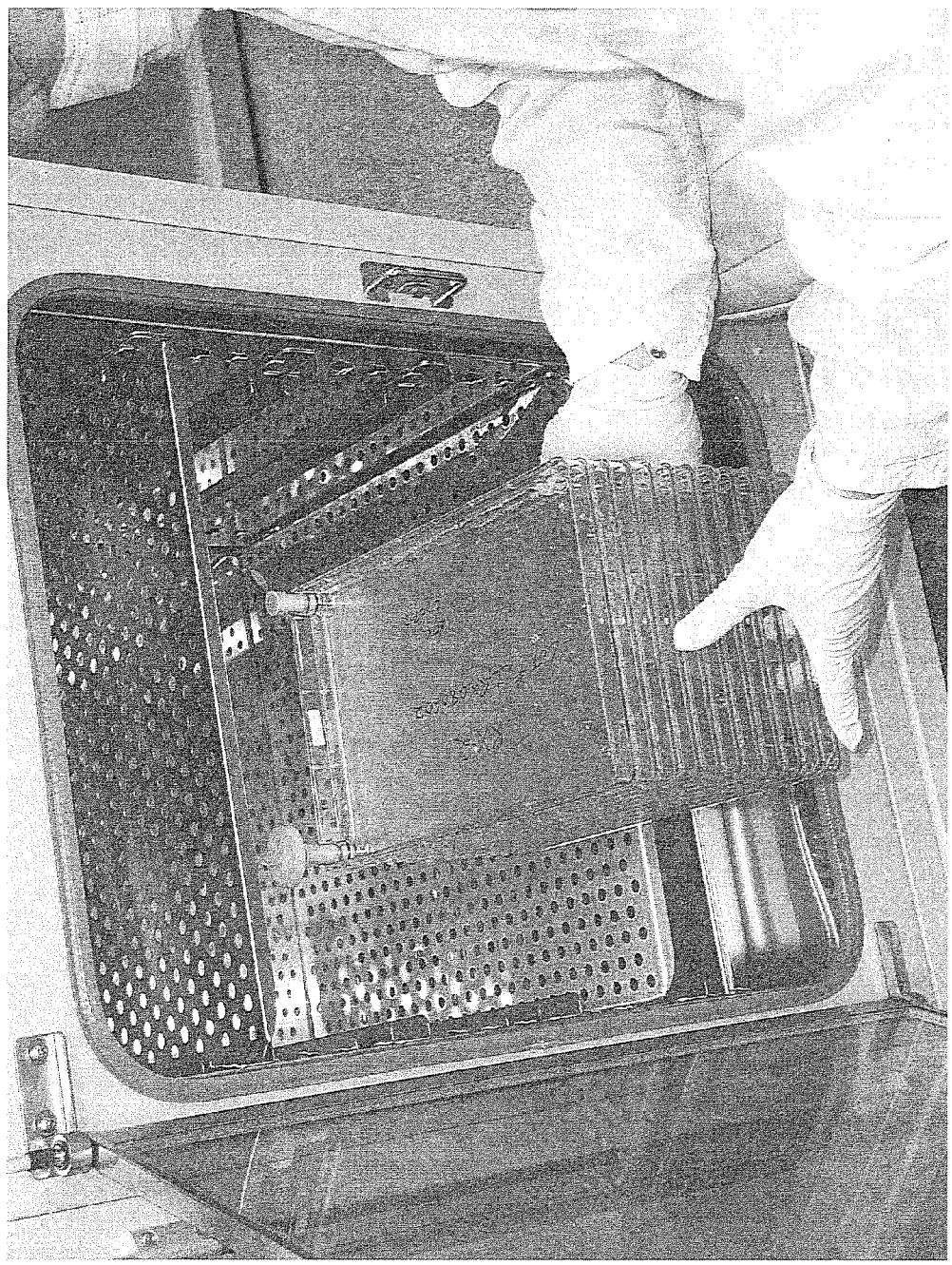
FIG. 9 is a photograph of the disposable cell culture device being placed in the incubator.

In the second step of the IRX-2 process, pooled MNCs are induced to produce biologically active cytokines by the addition of a mitogen, phytohemagglutinin (PHA), and ciprofloxacin. In conjunction with PHA, the ciprofloxacin stimulates the cells inducing transcription of type I cytokines including IL-2 and IFN-γ. FIG. 8 shows the cells being mixed with media/inducers and being transferred to a disposable cell culture device. FIG. 9 shows the disposable cell culture device being placed in the incubator. After induction, the induction mixture, culture medium and cells, is aseptically harvested and the cells are recovered via centrifugation. The cell culture device is washed with sterile saline three times and approximately 20% of the cells are recovered from the combined the washes with about 80% of the cells remaining attached to the CF surfaces. The recovered cells are then resuspended in fresh X-Vivo 10 culture medium with 80 μg/mL ciprofloxacin and returned to the cell culture device. Cytokine generation occurs over an additional 24 hr period producing the bulk IRX-2 free of mitogen.

To assess the efficiency of the wash process and assure minimal residual of the process impurity, the final bulk product is tested for residual PHA via an ELISA. The final product

TABLE 7

Cytokine production of IRX-2 produced using a Cell Processor ™ purified MNCs

| Description | IL-2 Bioactivity (IU/mL) | Cytokines ELISA (pg/mL) | | | |
|---|---|---|---|---|---|
| | | IL-1b | IL-2 | IFN-γ | TNF-α |
| Bulk (n = 5) | 560 ± 57 | 2,273 ± 402 | 21,428 ± 1880 | 6820 ± 2064 | 10,279 ± 2299 |
| Normalized (n = 5) | 184 ± 26 | 741 ± 111 | 7000 | 2261 ± 773 | 3350 ± 620 |
| QC Release Specification | 75-310 | 300-1400 | 4000-8000 | 1000-3800 | 1000-4300 |
| Manual | 76 | 418 | 5263 | 2028 | 1356 |
| Manual | 145 | 615 | 5797 | 1502 | 1815 |

Data presented as mean ± s.d specification for residual PHA is <150 ng/mL, the limit of detection of the PHA ELISA assay.

Figure 10:
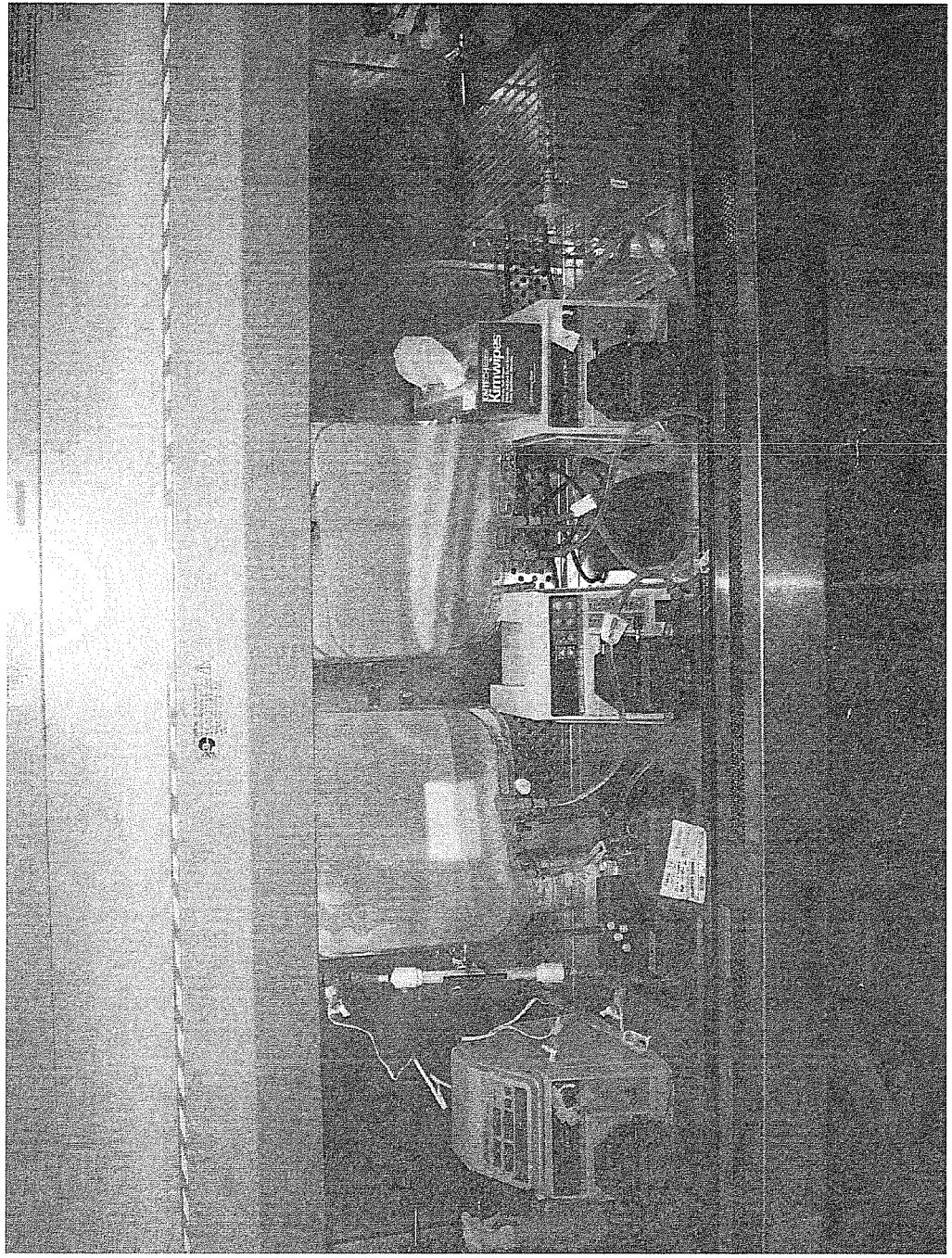
FIG. 10 is a photograph of cell washing with a Hollow Fiber filter.
Figure 11:
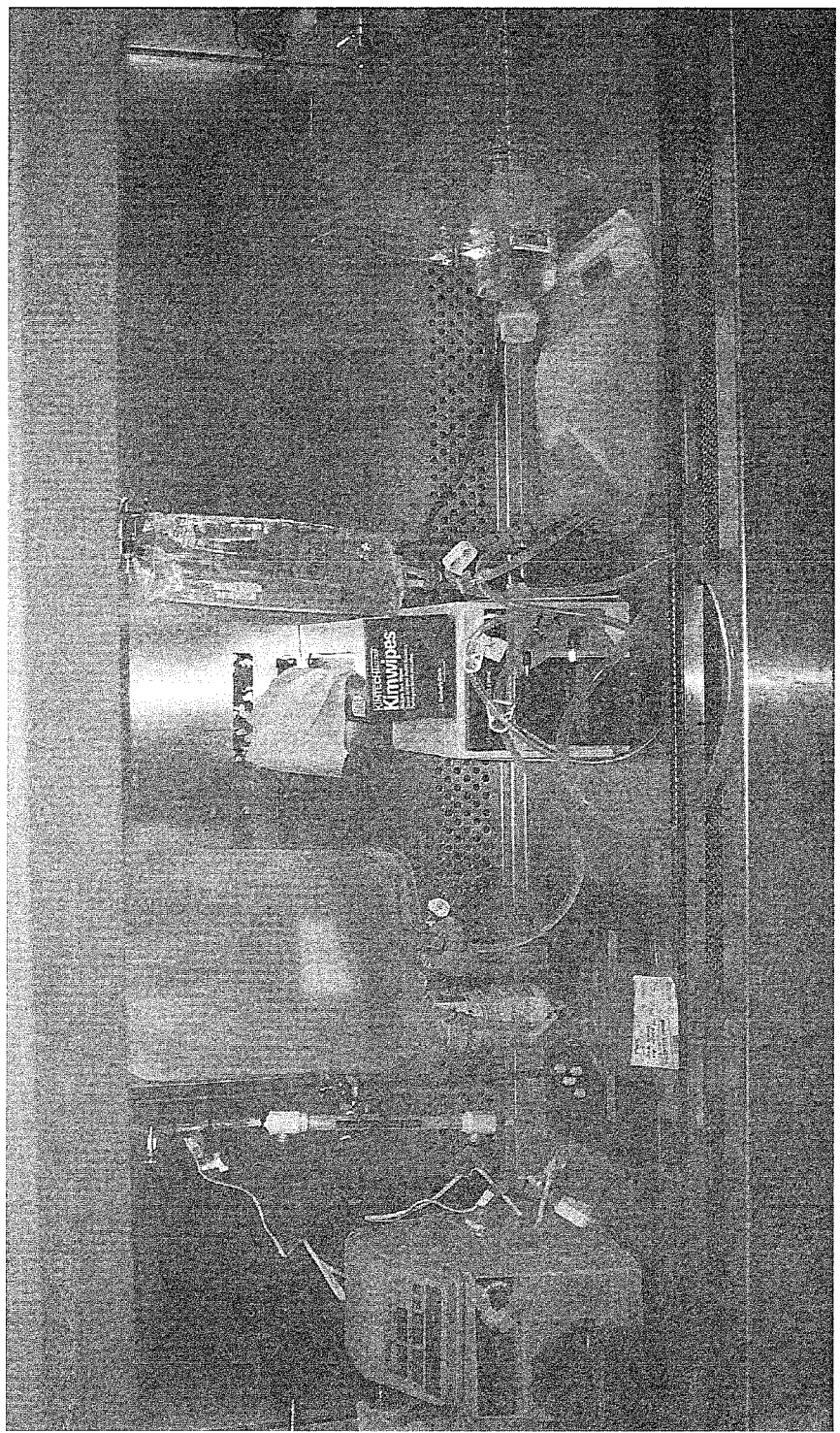
FIG. 11 is a photograph of cell washing with a Hollow Fiber filter.

In the improved method, cell washing and removal of PHA is accomplished using hollow fiber filtration in tangential flow mode as shown in FIGS. 10 and 11. In addition to cytokine production, the critical output parameters used to demonstrate equivalency are PHA removal and viable cell recovery.

Results:

To more accurately determine these low residual levels of PHA a new more sensitive PHA ELISA was developed and validated. Table 8 compares the PHA content of an IRX-2 Clinical lot processed using centrifugation (used in Phase II clinical production) with that for six lots in which washing was performed by the hollow fiber filtration method. With the new method, the mitogen has been removed to a level below the specification limit for PHA.

TABLE 9

Trypan Blue dye exclusion of recovered MNC during hollow fiber wash Viable Cell Count

| Sample Description | Total cells | % recovery |
|---|---|---|
| Total cell in reservoir Pre-PHA induction | $6.2 \times 10^9$ | 100 |
| CF Contents | $6.9 \times 10^8$ | 12 |
| $1^{st}$ wash | $4.5 \times 10^8$ | 7 |
| $2^{nd}$ wash | $1.9 \times 10^8$ | 3 |
| $3^{rd}$ wash | $2.8 \times 10^7$ | 1 |
| Total cells from wash steps | $1.3 \times 10^9$ | 23 |
| Recovered cell concentrate in XVG after wash and diafiltration | $1.5 \times 10^9$ | 24 |

Analysis of the cytokine produced by cells washed by the new method is presented in Table 10 show the typical IRX-2 cytokines.

TABLE 10

Cytokine production of IRX-2 produced using hollow fiber filtration

| Description | IL-2 Bioactivity IU/mL | Cytokine ELISA (pg/mL) | | | |
|---|---|---|---|---|---|
| | | IL-1b | IL-2 | IFN-γ | TNF-α |
| Phase II Manual Process | 204 | 899 | 10,470 | 2576 | 2264 |
| Hollow Fiber Mean ± s.d. N = 2 | 194 ± 58 | 1035 ± 858 | 11,999 ± 3984 | 2423 ± 858 | 5956 ± 3230 |

[1]Data presented as mean ± s.d

TABLE 8

PHA content following removal by centrifugation or hollow fiber filtration

| Batch | Batch Volume (mL) | Saline Wash volume | Wash Method | PHA concentration (ng/mL)* |
|---|---|---|---|---|
| Specification limit | N/A | N/A | N/A | <150 |
| Phase II Manual Process | 2800 | 1.8 L | Centrifugation | 104 |
| Hollow Fiber N = 6 | 2000-3500 | 2-3 L | Hollow fiber filtration | [1]91 ± 30 |

[1]Data presented as mean ± s.d assay date Nov. 06, 2006 Pre-MQ

Table 9 presents the % cell recovery of the washed cells using the HF washing method from two different batches. As can be seen below, the induction mixture recovered from the cell factory after the two hours incubation (labeled "CF Contents") contains a small fraction of the starting cells (12%) initially induced in the cell culture device. These data confirm, after the hollow fiber wash process, the cells were recovered with suitable viability and with minimal loss, well within assay variability, as determined by Trypan blue dye exclusion.

These preliminary data confirmed the Hollow Fiber (HF) filter system can be used to wash cells, replacing the arduous and time consuming manual centrifugation with adequate PHA removal, cell recovery and cytokine production in the production of IRX-2.

EXAMPLE 3

Harvest/Clarification of IRX-2 Culture Supernatant

Figure 12:
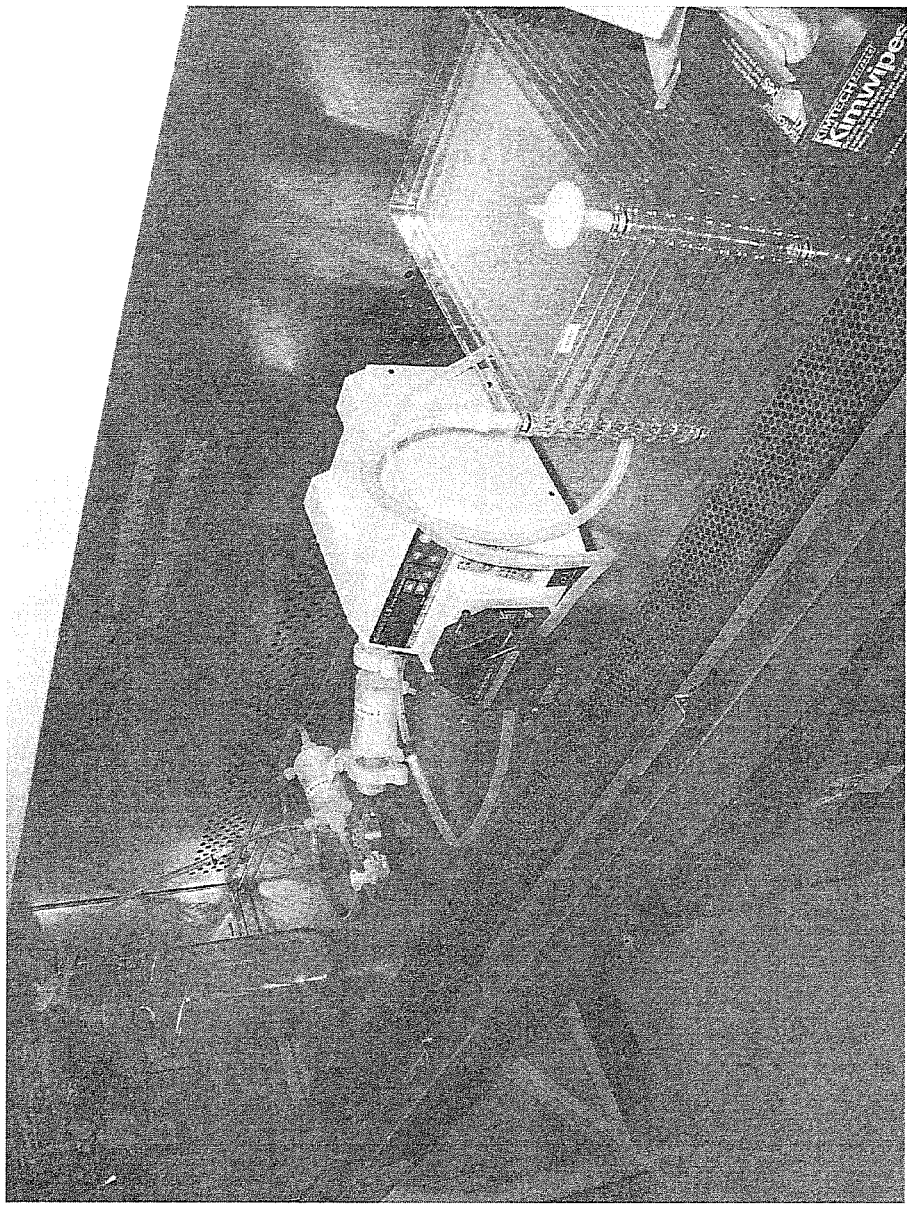
FIG. 12 is a photograph of supernatant clarification.

A supernatant clarification method was developed 0.45 micron filtration, which effectively removes cells from culture supernatant and is comparable to manual centrifugation without significantly reducing IRX-2 cytokine yields. There is shown to be little to no removal of critical IRX-2 cytokines. Supernatant clarification is shown in FIG. 12.

Results:

During the current IRX-2 process the culture supernatant containing the induced cytokines was clarified (i.e. cell removal) utilizing centrifugation. In order to streamline and scale-up the process we evaluated a 0.45 microfilter membrane filter for cell removal and supernatant clarification. The same PVDF membrane material is used in other stages of the IRX-2 process (anion exchange pre-filter and final product sterilizing grade filter) and was selected for minimal protein binding. Evaluation of the data demonstrates minimal cytokine removal when the IRX-2 culture supernatant was filtered through the fluorodyne membrane (Table 11). The filter will be scaled (using the batch volume to filter area ratio and at constant delta P) according to the required IRX-2 batch size.

TABLE 11

Cytokine % Recovery using 0.45 micron PVDF filtration

| | (% Recovery) | | | | |
|---|---|---|---|---|---|
| | IL-2 | | Cytokines ELISA | | |
| Sample | Bioactivity | IL-1β | IL-2 | IFN-γ | TNF-α |
| 0.45 micron PVDF (n = 3) | 101 ± 16 | 94 ± 8 | 96 ± 7 | 103 ± 13 | 92 ± 12 |

Mean ± sd

EXAMPLE 4

Feasibility Batches

The purpose of this study is to produce several batches at the current scale (2-3 L,) combining all of the new methods for IRX-2 production. This study will confirm that these automated, "scalable" methods for producing IRX-2 are comparable to the manual IRX-2 process.

Results:

Three feasibility batches were produced utilizing all of the process modification outlined in this application. Cytokine analysis of the IRX-2 product utilizing the entire modified process is presented in Table 12. These batches were normalized to a target IL-2 concentration of 7000 pg/mL and compared to two clinical lots produced by the manual process. Analysis of these batches showed the new process did produce IRX-2 in the typical cytokine ranges.

TABLE 12

Cytokine Analysis of IRX-2 Produced by Commercial Process

| | IL-2* Bioactivity | Cytokines ELISA (pg/mL)* | | | |
|---|---|---|---|---|---|
| Description | (IU/mL) | IL-1b | IL-2 | IFN-γ | TNF-α |
| Commercial Process N = 3 | 322 ± 120 | 1933 ± 559 | 15,416 ± 6973 | 3349 ± 1899 | 4856 ± 2117 |
| Commercial Normalized Commercial Process N = 3 | 152 ± 29 | 939 ± 203 | 7000 | 1504 ± 293 | 2216 ± 61 |
| Clinical Manual Phase I | 76 | 418 | 5263 | 2028 | 1356 |
| Manual Phase II | 145 | 615 | 5797 | 1502 | 1815 |

PHA removal via the hollow fiber washing method was also confirmed to provide acceptable product with PHA levels meeting the QC release specification of <150 ng/mL (Table 13) and provides a typical dose of 50 ng/kg, well below the level of safe administration (167 ng/kg) or toxicity level (833,000 ng/kg) by 4 orders of magnitude. This clearly demonstrates the low levels of the residual process mitogen represent a safe product.

TABLE 13

PHA content following removal by centrifugation or hollow fiber

| Description | Batch Volume (mL) | Saline Wash volume | Wash Method | PHA concentration (ng/mL)* |
|---|---|---|---|---|
| Specification limit | N/A | N/A | N/A | <150 |
| Phase II Manual Process | 1500 | 1.2 L | Centrifugation | 63 |
| HF N = 3 | 2500-3500 mL | 4-5 L | Hollow fiber filtration | 64 ± 7 |

*Prior to anion exchange chromatography and viral filtration

Figure 13:
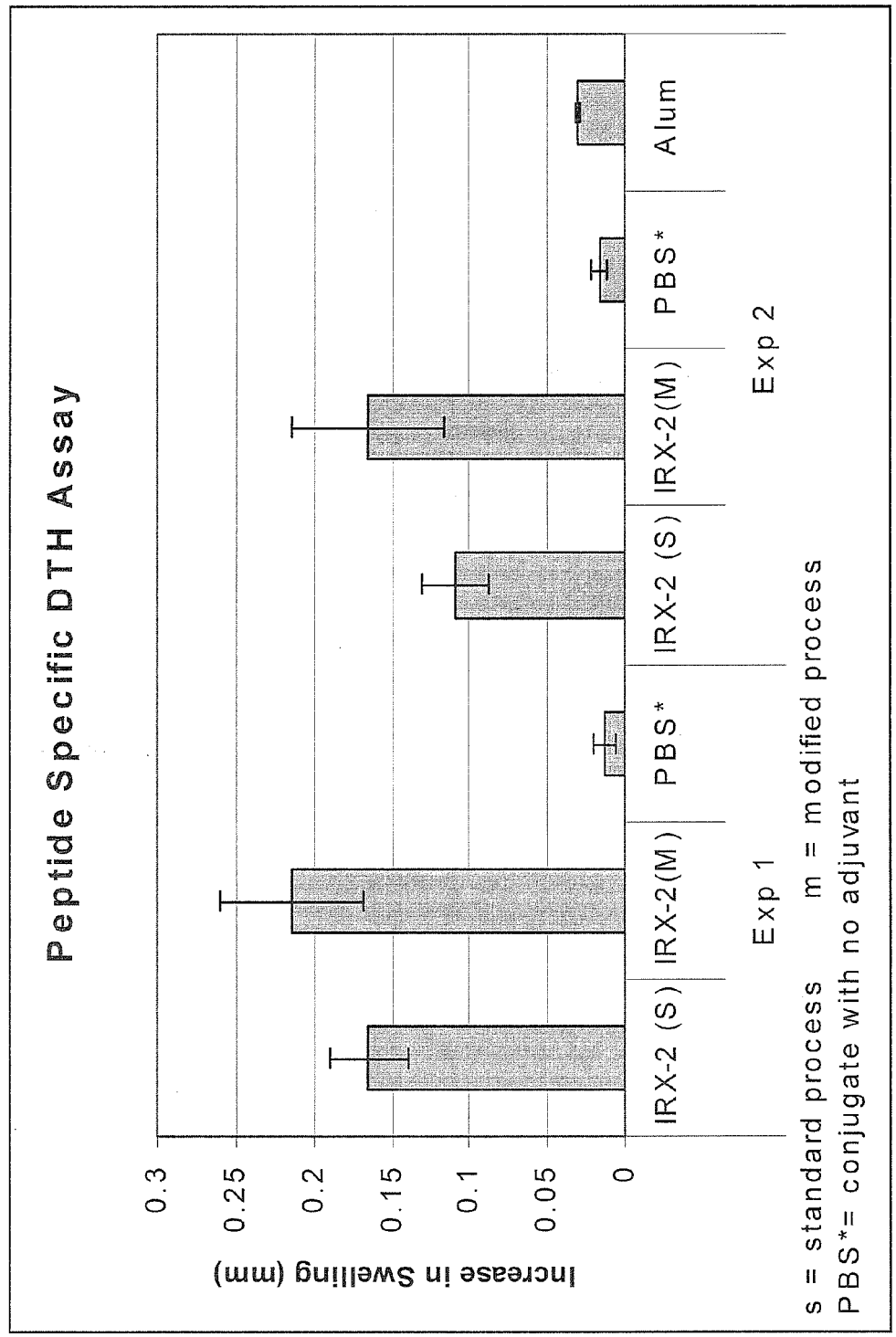
FIG. 13 is a graph of specific peptide DTH assay.

In addition to analytical testing, IRX-2 produced by the modified process also showed equivalence performance in an in vivo model, the peptide conjugate vaccine model. IRX-2 has been shown to illicit a T-cell response in mice as measured by the generation of cytotoxic T cells or delayed type hypersensitivity, DTH (Naylor and Hadden 2003). Samples of both the manual process and IRX-2 made by the commercial process both induced delayed type hypersensitivity reaction (DTH) in mice using PSMA peptide—KLH conjugate as antigen (Table 14 and FIG. 13). This confirms equivalent biological performance in an in vivo model and provides data supporting the comparability of the IRX-2 made by the modified process.

TABLE 14

In Vivo Activity Studies Evaluating Manual Process IRX-2 vs Commercial Process IRX-2

| IRX-2 | ELISA Cytokine (pg/mL) | | | | |
| --- | --- | --- | --- | --- | --- |
| Sample | IL-2 | IL-1b | IFN-g | TNF-a | IL-8 |
| Phase II Manual | 5797 | 516 | 1502 | 1815 | 49180 |
| Manual | 6870 | 403 | 1688 | 1798 | 34824 |
| Commercial) (Experiment 1) | 7000 | 667 | 2544 | 3917 | 46671 |
| Commercial (Experiment 2) | 7000 | 667 | 2544 | 3917 | 46671 |

Protocol: Mice were immunized with PSMA-KLH conjugate vaccine and IRX-2 prepared either by the standard process or the modified process. Mice received 9 additional injection of IRX-2 alone and were boosted on day 14 and 28. The DTH response to the peptides was measured as increase in footpad swelling 9 days after the booster immunization.

Conclusion

The data herein show that the IRX-2 process is significantly improved by the proposed process improvements: (1) MNC purification using the automated cell processor, (2) storage of MNCs in FEP bags, (3) cell washing using Hollow Fiber (HF) filter system, (4) cytokine induction and generation in a disposable cell culture device, and (5) culture supernatant clarification via filtration using PVDF 0.45 μm filter. An assessment of each unit operation and its changes shows that the critical parameters are maintained within an acceptable working range and that the process is able to provide product meeting its specifications. The process was further evaluated by performing several batches with all of the process modifications which produced all of the IRX-2 cytokines in typical ratios as previously seen with the current process. Comparability of the primary cell derived biologic components and biological equivalence were confirmed by the RAYBIO Human Cytokine Antibody Array (RayBiotech, Inc.) and the peptide conjugate vaccine model. Based on these data, the modified process is comparable to the current IRX-2 process and producing a consistent and reproducible product. A summary of the changes can be found in Table 21 further below.

EXAMPLE 5

Virus Elimination

Figure 14:
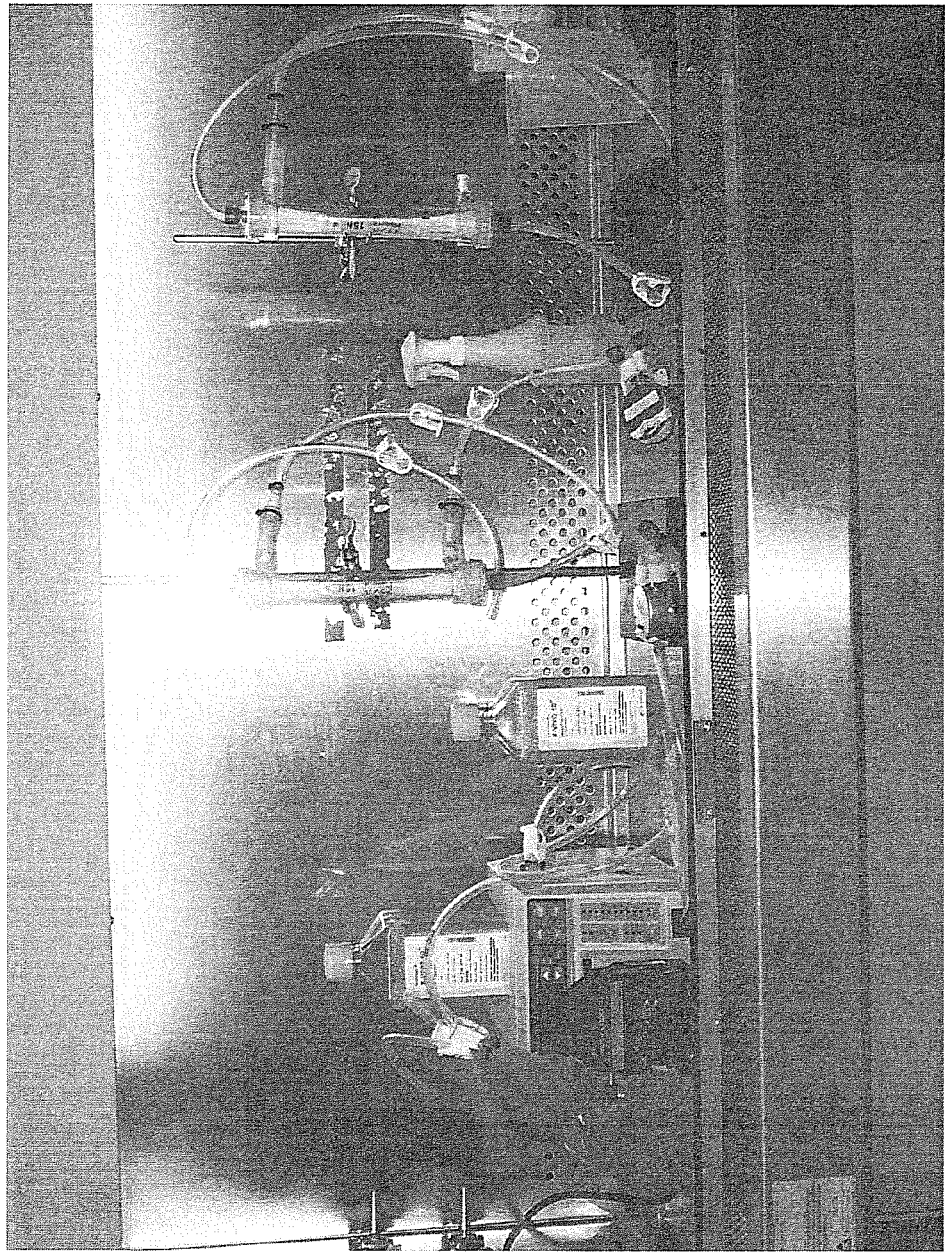
FIG. 14 is a photograph of virus filtration.
Figure 15:
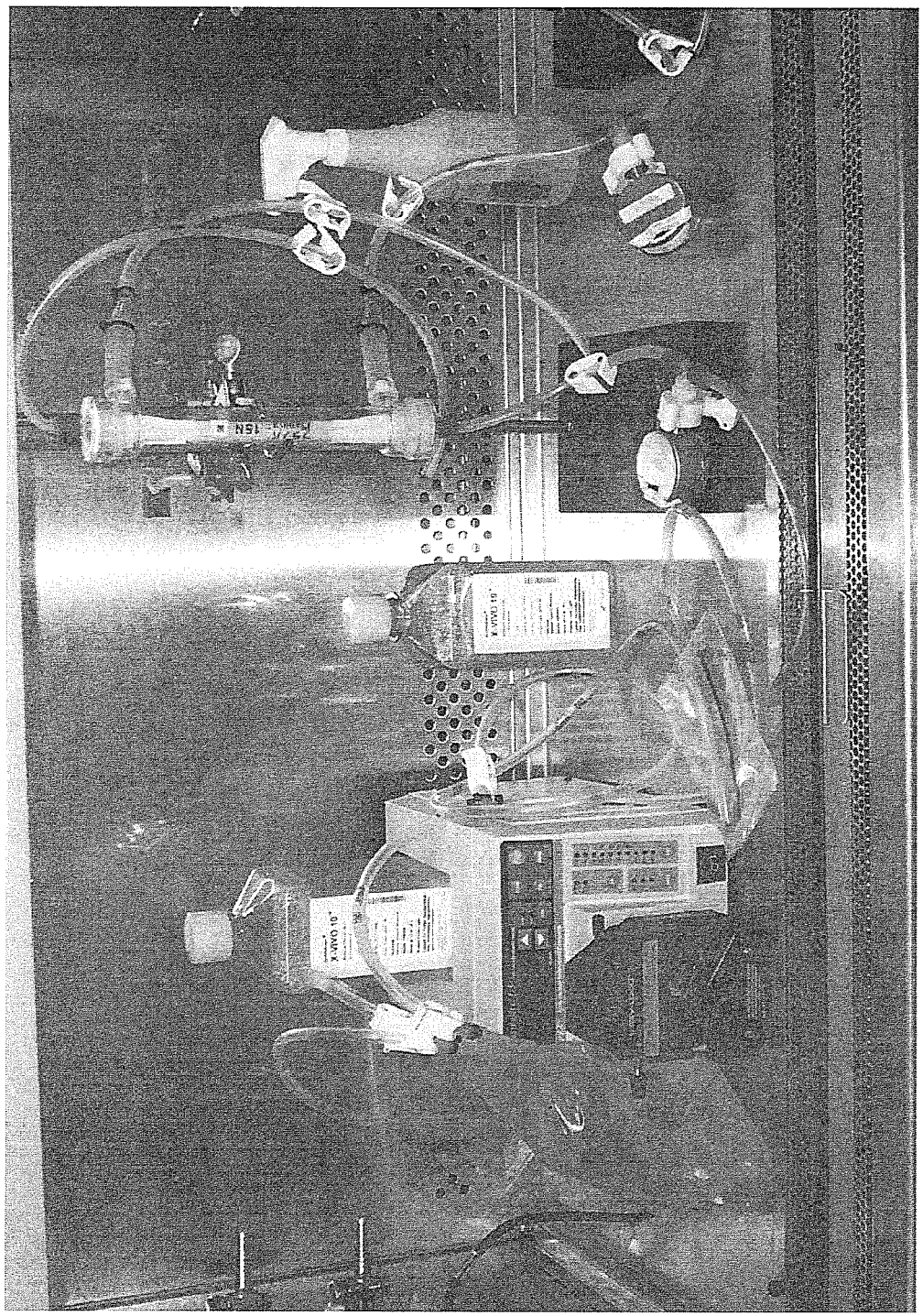
FIG. 15 is a photograph of virus filtration.
Figure 16:
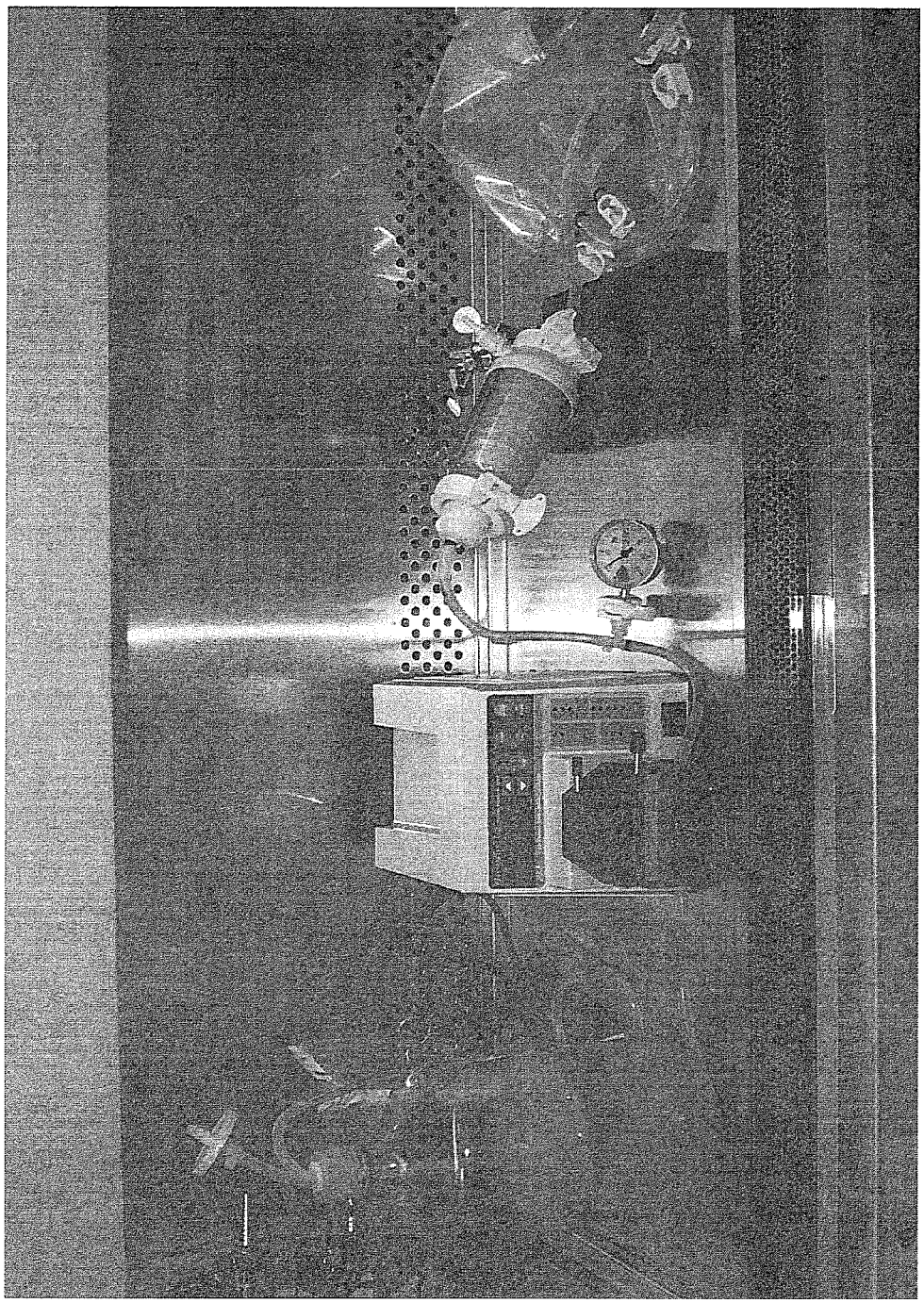
FIG. 16 is a photograph of virus removal though a disposable anion exchange chromatography unit.

As stated above, the previous method of IRX-2 manufacture includes viral clearance by nanofiltration using dual 15N filters in series as a dedicated virus removal step (shown in FIGS. 14 and 15) and also includes DNA removal by the (MQ) disposable anion exchange chromatography unit (shown in FIG. 16).

UVC Treatment

Figure 17:
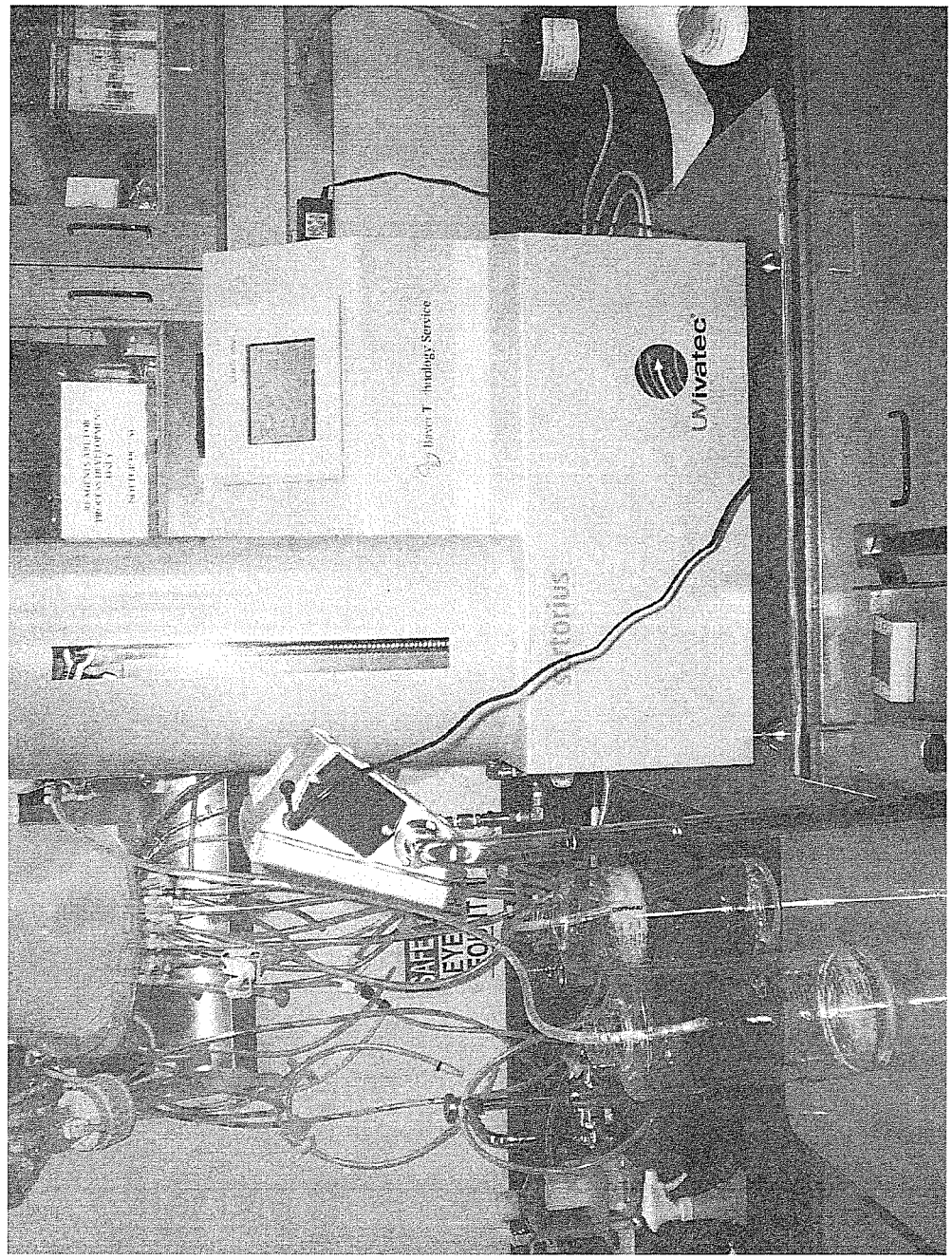
FIG. 17 is a photograph of viral inactivation through UVC.
Figure 18:
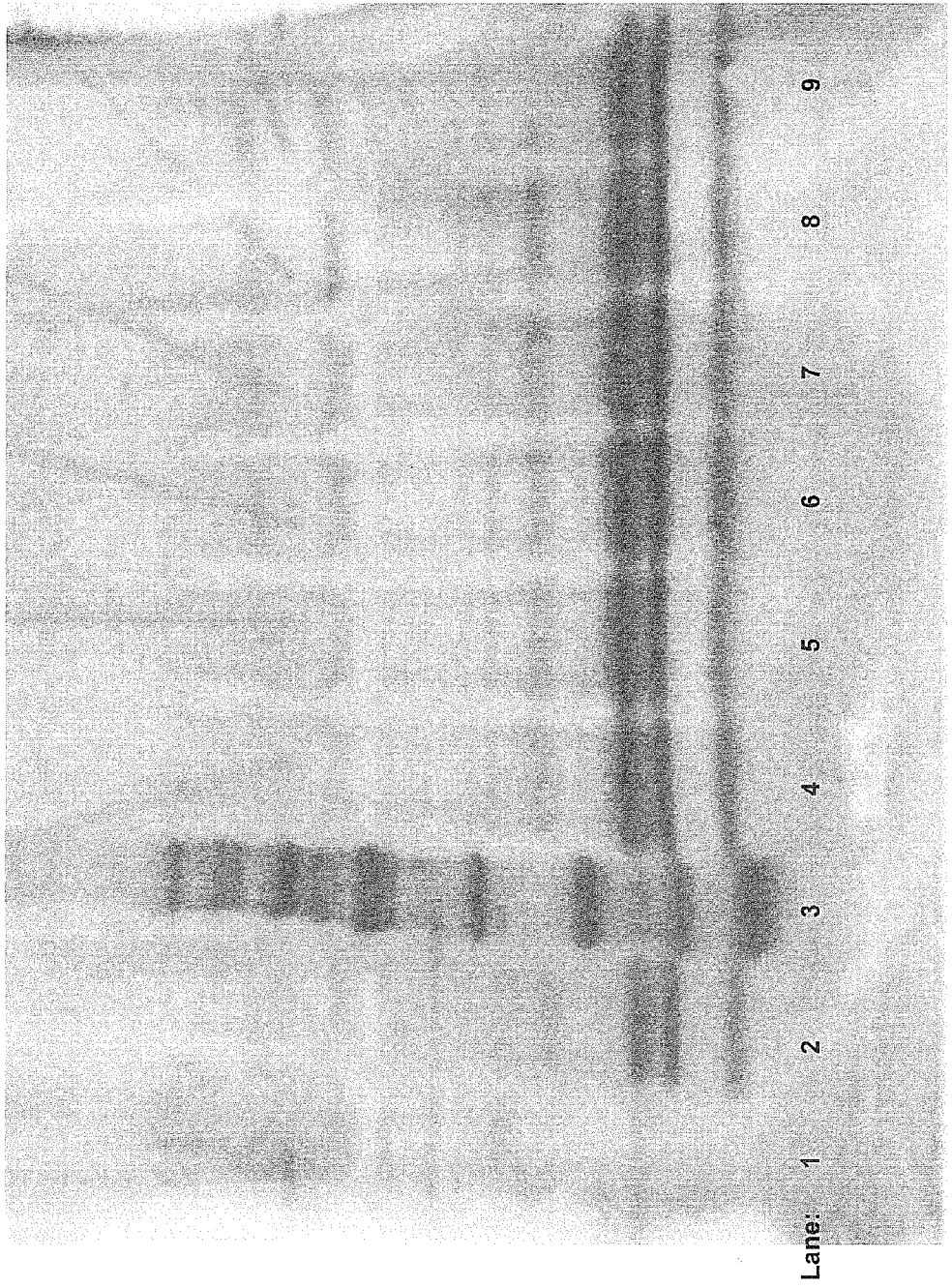
FIG. 18 is a photograph of a Western Blot Analysis of the primary cell derived biologic after UVC.

The UVC system, a reactor with a novel spiral flow hydraulic mixing and shown in FIG. 17, was designed to overcome these limitations and to target application for use in biotechnology products (Schmidt et al. 2005; Schmidt and Kauling, 2007). Studies with the UVC demonstrated the effectiveness of UVC treatment, in the novel reactor, to inactivate viruses without causing significant protein damage (Wang et. al. 2004). Virus and mock spiked Alpha$_1$-proteinase inhibitor (Alpha$_1$ PI) solutions were tested with various doses of UVC. The virus samples were assayed for residual infectivity and amplified by the polymerase chain reaction (PCR). The mock spiked samples were also assayed for protein integrity. Alpha$_1$ PI, a plasma protein was selected as the target protein due to the presence of UV-absorbing amino acids by which UV induced damage could be easily detected by a decrease in biological activity. A diverse panel of viruses including enveloped and non-enveloped viruses with single-stranded or double stranded, long or short, RNA or DNA genomes was tested. UVC treatment of Alpha$_1$-PI resulted in over 4 log$_{10}$ inactivation of SV40, PPV, HAV, Sindbis, Reo and Adeno viruses demonstrating all test viruses were inactivated regardless of the type of nucleic acid or presence of an envelope.

In this study, viruses with the smallest genomes were found to be those most sensitive to UVC treatment and detection of PCR amplicons $\geq 2.0$ kb was correlated to viral infectivity. Doses that achieved significant virus inactivation yielded recovery of >90% protein activity even in the absence of quenchers. The kinetics of viral inactivation were relatively linear and no small resistant fraction of virus persisted. In addition, PPV was shown to be a suitable model for B19 in UV irradiation studies by both PCR and infectivity assays. A summary of the process development for the UVC treatment is listed in Table 22 further below.

UVivatec® UVC System.

In the UVC reactor, novel hydraulic spiral flow along an irradiation source inducing highly efficient mixing in a fluid stream, so high doses of UVC irradiation can be delivered evenly and uniformly throughout the solution thus the required residence times in the irradiation chamber are extremely short and UVC treatment is controllable (Wang et. al., 2004; Schmidt et al., 2005; Schmidt and Kauling, 2007). A tubular poly(tetrafluorethelene) conduit that spirals around a quartz tube with a concentric UVC source (254 nm) forms the irradiation chamber of the reactor (FIG. 38). As fluid streams move spirally along the lamp secondary circulating flows (Dean vortices) are generated that provide highly efficient mixing which optimize virus exposure to the UV light source and allow for uniform and controllable irradiation of the entire volume.

To optimize the virucidal activity of the UVC and minimize protein damage the UVC system utilizes UVC irradiation at a wavelength of 254 nm. This wavelength was selected to specifically target the nucleic acid component of the virus. FIG. 39 illustrates how viruses are inactivated at this wavelength while proteins are relatively unaffected (Schmidt et. al. 2007).

In addition, doses required to inactivate viruses is 10 times lower than previous described for UV irradiation used for plasma product, 1000-2000 J/m$^2$ (Chin et. al. 1995, Chin et. al. 1997, Caillet-Fauquetet. al. 2004, Sugawara et. al. 2001).

UVC dosage is typically described in units of UV fluency and is dependent on (1) average irradiance emitted by the lamp (2) residence time in the irradiation chamber and (3) the optical density of the test solution, (W s/cm2=J/cm2) (Wang et. al., 2004; Li et. al. 2005). Prior to UVC treatment, the solution's $A_{254}$ is measured to determine the interference generated by the protein solution and based on the $A_{254}$ the required flow rate to achieve the required dose is calculated.

Viral Clearance Studies

The IRX-2 commercial process includes two validated viral clearance methods shown to remove or inactivate up to 11 log$_{10}$ of adventitious viral contamination (i.e. anion exchange chromatography and 15 nm filtration). A third method, UV virus inactivation (UVC), was evaluated for use in the IRX-2 process. Consistent with previously published data with the UVC technology (Wang et. al., 2004; Schmidt et al., 2005; Schmidt and Kauling, 2007), doses known to kill adventitious non-enveloped viruses, up to 150 J/m$^2$, show minimal inactivation of the IRX-2 cytokines.

The dose of 100 J/m² was shown to inactivate 4 logs of several target viruses including PPV, and HAV (Wang et. al., 2004; Schmidt et al., 2005; Schmidt and Kauling, 2007) and was shown to have minimal effect on IRX-2 cytokines. It was therefore selected as the target dose for IRX-2.

The choice of viruses used for this study was based on the nature and origin of the starting material and raw materials used in production (i.e., biotech product derived from human leukocytes). Each virus used is a relevant virus that may contaminate the source material (in this case human blood) or a recognized model for the expected contaminating species. In addition, the model viruses were selected for their ability to grow and create a high titer stock (in serum-free or low protein medium) and their ease of detection in a sensitive and reliable assay. The viruses used for this study were: HIV-1, BVDV, HAV, and PPV. The viruses used represent a wide range of physico-chemical properties in order to thoroughly test the ability of the UVC systems to eliminate viruses. It was not expected that UVC in these low dose ranges <100 J/m² would be effective against larger enveloped viruses. Therefore, pseudorabies virus (PRV), typical surrogate for large, enveloped DNA viruses was not tested in this preliminary study.

The viral clearance capability of UVC in IRX-2 was confirmed in two viral clearance studies. Sample of IRX-2 (approximately 50 ml) was spiked with model and blood borne viruses and exposed to UVC doses ranging from 40-150 J/m². Table 15 shows the results at 100 J/m² and demonstrated UVC technology can provide 4 $\log_{10}$ of inactivation of viruses.

TABLE 15

Viral Clearance Summary

| | $\text{Log}_{10}$ Viral Clearance | | | |
|---|---|---|---|---|
| Virus Type | Mustang-Q | Dual 15 N | UVC* | Total |
| PPV | 4.30 | ≧7.24 | 7.37 | ≧18.9 |
| HIV-1 | ≧4.39 | ≧4.18 | 1.93 | ≧10.5 |
| HAV | ND+ | >5.28 | 5.90 | ≧11.2 |
| BVDV | ND+ | >6.01** | 5.31 | ≧11.3** |
| PRV | ≧4.5 | ≧6.45 | nd+ | ≧10.9 |

100 J/M²;
**Calculated from a single 15N filter;
+Not determined

Under scaled down process conditions, UVC demonstrated over 4 $\log_{10}$ viral clearance for three of the viruses tested, PPV, HAV & BVDV. Over 7 logs of PPV were inactivated with UVC. PPV, a model for B-19, is one of the smallest and most difficult viruses to inactivate by other methods, solvent/detergent, pH or heat (Chin et. al., 1995). Recent studies have confirmed the suitability of PPV to be a suitable model for B-19 in parallel comparison during UVC inactivation (Wang et. al., 2004). Human parvovirus, B-19, can reach >$10^{12}$ IU/mL in human plasma and is a potential hazard for blood derived products (Doley and Corcoran 2006). HIV-1 was less efficiently inactivated by UVC, 1.9 logs, possibility due to its larger genome size (80-110 nm), which potentially makes it more difficult to inactivate with UVC (Wang et. al., 2004) but when added to the IRX-2 process increases the viral clearance to over 10 $\log_{10}$.

This study validates the effectiveness of the UVC step for the IRX-2 process. In addition, the UVC demonstrated over 4 logs removal of PPV, HAV and BVDV, thus providing an additional viral clearance step in the IRX-2 process. With the addition of UVC, the data indicates the total clearance through the cumulative validated process steps was shown to be ≧10.5 logs for HIV-1, ≧11.2 for HAV, ≧11.3 for BVDV and ≧18.9 logs for PPV.

2-3 L Batch UVC

To fully evaluate the UVC system, four batches were prepared using the new process including all the combined process changes including processing with UVC (Table 16).

TABLE 16

Percent recovery of IRX-2 during UVC at the Commercial Scale

| % Recovery | TNF-α | IL-2 | Cytokines (pg/ml) | | | | | | | | |
|---|---|---|---|---|---|---|---|---|---|---|---|
| @100 J/m2 | IU/mL | IU/mL | IL-1β | Il-2 | IFN-γ | TNF-α | IL-8 | IL-6 | Il-10 | G-CSF | GM-CSF |
| mean | 93 ± 19 | 88 ± 6 | 96 ± 7 | 90 ± 5 | 107 ± 10 | 92 ± 21 | 95 ± 3 | 66 ± 21 | 95 ± 32 | 96 ± 32 | 89 ± 7 |

Results:

UVC treatment of lab scale batches produced at the current scale, 2-3.5 L showed less detectable loss of TNF-α bioactivity with a mean percent recovery of TNF-α bioactivity of 93% and 92% by ELISA, thus confirming the original findings in the small scale studies, namely that IRX-2 is not affected by UVC irradiation under these conditions. All other cytokines by ELISA or bioassay (CTLL-2) showed very good recovery of IRX-2 cytokines at a dose of 100 J/m² which effectively inactivated non-enveloped viruses, HAV and PPV.

Figure 19:
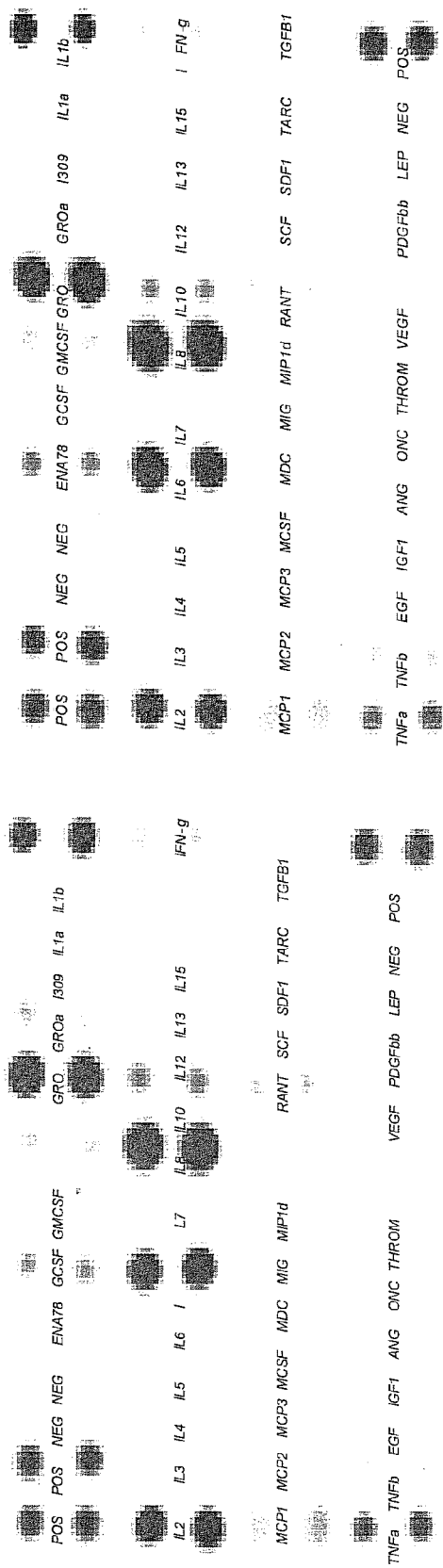
FIG. 19 is a photograph of a cytokine array of the primary cell derived biologic before and after UVC.

Array analysis, Ray Biotech, of the most common cytokines (Huang et. al. 2001) on IRX-2 from UVC processed IRX-2 revealed IRX-2 product looks comparable in cytokine composition before and after UVC treatment (FIG. 19).

Conclusion

Figure 20:
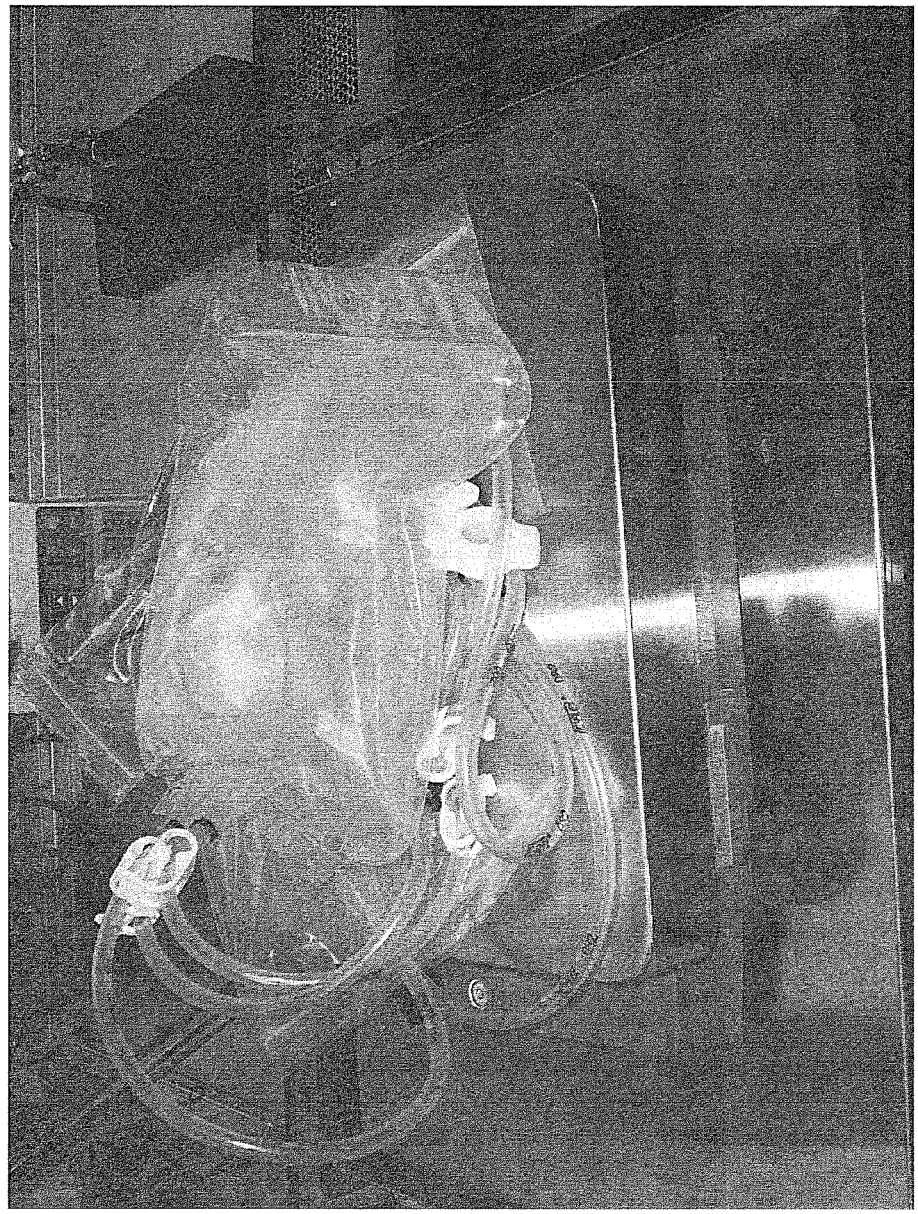
FIG. 20 is a photograph of bulk primary cell derived biologic ready for freezing.

The data herein show that the IRX-2 process is significantly improved by the proposed process addition of UVC inactivation and can be validated as a viral inactivation method. The addition of an inactivation step meets the regulatory requirements and adds to the robust viral inactivation/removal methods currently in the IRX-2 process. Assessment of this unit operation and its changes shows that the critical parameters are maintained within an acceptable working range and that the process is able to provide product meeting its specifications. After UVC inactivation, the IRX-2 bulk product can be frozen (shown in FIG. 20) and prepared for distribution to patients.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of making a primary cell derived biologic, including the steps of:
   (a) removing contaminating cells from mononuclear cells (MNCs) by loading leukocytes onto lymphocyte separation medium (LSM), and washing and centrifuging the medium with an automated cell processing and washing system;
   (b) storing the MNCs overnight in a closed sterile bag system;
   (c) stimulating the MNCs with a mitogen and ciprofloxacin in a disposable cell culture system to produce cytokines;
   (d) removing the mitogen from the mononuclear cells by filtering;
   (e) incubating the filtered MNCs in a culture medium;
   (f) producing a clarified supernatant by filtering the MNCs from the culture medium;
   (g) producing a chromatographed supernatant by removing DNA from the clarified supernatant by anion exchange chromatography; and
   (h) removing viruses from the chromatographed supernatant by filtering with dual 15 nanometer filters in series, thereby producing a primary cell derived biologic, wherein the primary cell derived biologic comprises IL-1β, IL-2, and IFN-γ.

2. The method of claim 1, wherein step (a) further comprises removing contaminating cells from MNCs from multiple donors simultaneously.

3. The method of claim 1, wherein step (a) further comprises centrifuging at 1500 to 3000 rpm for 20 minutes to optimize removal of granulocytes and red blood cells.

4. The method of claim 1, wherein the mitogen is phytohaemagglutinin (PHA).

5. The method of claim 4, wherein step (d) comprises lowering the level of PHA to less than 150 ng/mL.

6. The method of claim 5, wherein step (d) comprises filtering in tangential flow mode.

7. The method of claim 1, wherein step (d) comprises filtering in tangential flow mode.

8. The method of claim 1, wherein the incubation in a culture medium is for 24 hours.

9. The method of claim 1, wherein the filter of step (f) is a 0.45 micrometer filter.

10. The method of claim 1, wherein step (h) further comprises applying ultraviolet-C (UVC) light to the chromatographed supernatant to clear the chromatographed supernatant of adventitious agents.

11. The method of claim 10, wherein the UVC is applied uniformly by spirally flowing the chromatographed supernatant along an UVC irradiation source.

12. The method of claim 1, wherein the ciprofloxacin is present in an amount of 80 micrograms/mL in step (c).

13. The method of claim 1, wherein the culture medium of step (e) includes 80 micrograms/mL of ciprofloxacin.

14. The method of claim 1, wherein the purified mononuclear cells (MNCs) in step (a) have a granulocyte content below 5%.

15. The method of claim 1, wherein step (a) further comprises removing platelets to a level of below $1.2 \times 10^{10}$ cells.

16. The method of claim 1, wherein the primary cell derived biologic comprises the cytokines IL-1β, IL-2, IL-6, IL-8, TNF-α and IFN-γ.

17. The method of claim 1, wherein at least 4 L of the primary cell derived biologic is produced.

* * * * *